United States Patent
Chiniquy et al.

(10) Patent No.: US 10,233,457 B2
(45) Date of Patent: Mar. 19, 2019

(54) INHIBITION OF A XYLOSYLTRANSFERASE TO IMPROVE SACCHARIFICATION EFFICIENCY

(71) Applicant: The Regents of the University of California, Oakland, CA (US)

(72) Inventors: Dawn Chiniquy, Berkeley, CA (US); Pamela Ronald, Davis, CA (US); Henrik Vibe Scheller, Millbrae, CA (US)

(73) Assignee: The Regents of the University of California, Oakland, CA (US)

( * ) Notice: Subject to any disclaimer, the term of this patent is extended or adjusted under 35 U.S.C. 154(b) by 665 days.

(21) Appl. No.: 13/953,642

(22) Filed: Jul. 29, 2013

(65) Prior Publication Data

US 2014/0033365 A1 Jan. 30, 2014

Related U.S. Application Data

(60) Provisional application No. 61/676,536, filed on Jul. 27, 2012.

(51) Int. Cl.
*C12N 15/82* (2006.01)
*A01H 5/10* (2018.01)

(52) U.S. Cl.
CPC ........... *C12N 15/8246* (2013.01); *A01H 5/10* (2013.01)

(58) Field of Classification Search
None
See application file for complete search history.

(56) References Cited

U.S. PATENT DOCUMENTS

2004/0146904 A1* 7/2004 Phillips .............. C12N 15/8226
   435/6.12
2010/0143915 A1* 6/2010 Ronald .............. C12N 15/8245
   435/6.14

OTHER PUBLICATIONS

Strasser et al, FEBS Letters (2004) 561: 132-136.*
Singh et al 2010, Plant Science 179: 114-122.*
Chen et al 2007 Nature Biotechnology 25(7): 759-761.*
Piston et al 2010 Planta 231: 677-691.*
Anders, N., et al., "Glycosyl transferases in family 61 mediate arabinofuranosyl transfer onto xyland in grasses" *PNAS* (2012) 109(3): 989-993.
Cao, P.J., et al., "Construction of a rice glycosyltransferase phylogenomic database and identification of rice-diverged glycosyltransferases", *Molecular Plant* (2008) 1(5): 858-877.
Mitchell, R.A.C., et al., "A novel bioinformatics approach identifies candidate genes for the synthesis and feruloylation of arabinoxylan", *Plant Physiology* (2007) 144: 43-53.
Naran, R., et al., "Novel rhamnogalacturonan I and arabinoxylan polysaccharides of flax seed mucilage", *Plant Physiology* (2008) 148: 132-141.
Piston, F., et al., "Down-regulation of four putative arabinoxylan feruloyl transferase genes from family PF02458 reduces ester-linked ferulate content in rice cell walls", *Planta* (2010) 234: 677-691.

* cited by examiner

*Primary Examiner* — David H Kruse
(74) *Attorney, Agent, or Firm* — Kilpatrick Townsend & Stockton LLP

(57) ABSTRACT

The invention provides compositions and methods for inhibiting the expression of the gene XAX1 in grass plants. Plants with inhibited expression of XAX1 have use, e.g., in biofuel production by increasing the amount of soluble sugar that can be extracted from the plant.

12 Claims, 6 Drawing Sheets

Specification includes a Sequence Listing.

INHIBITION OF A XYLOSYLTRANSFERASE TO IMPROVE SACCHARIFICATION EFFICIENCY

CROSS-REFERENCE TO RELATED APPLICATIONS

This applications claims priority benefit of U.S. provisional application No. 61/676,536, filed Jul. 27, 2012, which application is herein incorporated by reference for all purposes.

STATEMENT AS TO RIGHTS TO INVENTIONS MADE UNDER FEDERALLY SPONSORED RESEARCH AND DEVELOPMENT

This invention was made with government support under DE-AC02-05CH11231 awarded by the United States Department of Energy. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-107-1.TXT, created on Jul. 29, 2013, 34,296 bytes, machine format IBM-PC, MS-Windows operating system, is hereby incorporated by reference in its entirety.

BACKGROUND OF THE INVENTION

Xylans are polysaccharides present in the cell walls of all plants. They comprise the major non-cellulosic component of secondary walls of angiosperms. Hence, xylans are quantitatively second only to cellulose in biomass on earth. Xylans are valuable components of human and animal nutrition, constituting a major component of dietary fiber in cereals (1). The amount of xylan as well as its chemical composition is an important element of bread-making, influencing dough yield, flavor and shelf life (2). Xylan is of particular interest for the improvement of feedstocks for the generation of cellulosic biofuels, a currently expensive and inefficient process (3). Xylan inhibits access of cellulases to cellulose, and xylan is an additional substrate for cross-linking to lignin.

Xylans play an important structural role in plant cell walls, presumably through interactions with cellulose microfibrils and other components of the wall (4, 5). While the organization of these various components in the cell wall is not well understood, the increased cross-linking apparently contributes to the recalcitrance of the cell wall (6, 7). Xylans are structurally diverse between taxonomic groups (4). The most basal form of xylan is a main chain that lacks substitutions as seen in the green algae *Caulerpa* that has β-1,3-D-xylose in place of cellulose, and the red seaweeds *Palmariales* and *Nemaliales* that have a mixed linkage β-(1,3-1,4)-D-xylose backbone (8). Xylans of embryophytes have a β-1,4-linked xylose backbone. Xylans found in dicots are mostly restricted to the secondary cell walls, and hence a main component of wood. Dicot xylans are commonly substituted with α-(1→2)-linked glucuronosyl and 4-O-methyl glucuronosyl residues (1). Xylan in birch, spruce, and *Arabidopsis* have been found to contain the reducing end oligosaccharide β-D-Xylp-(1→4)-β-D-Xylp-(1→3)-α-D-GalpA-(1→4) D-Xylp (9-11) which, interestingly, has not been found in the xylan of grasses. Commelinid monocot xylans are unique from dicots and other monocots. This group, which includes the grasses, contains xylan as the main non-cellulosic component in both the primary and secondary cell walls. These xylans have very little glucuronic acid, but are mostly substituted with α-1,2 and α-1,3 arabinosyl residues. A unique feature of grass xylans is the ferulate and coumarate esters attached to some of the α-1,3 arabinosyl residues. These ferulate esters mediate intra- and intermolecular cross-linking, possibly increasing the strength of the cell wall (7). Another feature that makes grass xylan unique is the β-1,2 linked xylose residues found on these feruloyl-arabinofuranose substitutions (12-16).

During the past six years, there has been significant progress made toward identifying the glycosyltransferases (GTs) that synthesize xylan. The irregular xylem (irx) mutants, named for their collapsed xylem vessels due to their secondary cell wall deficiency, have been instrumental in elucidating the mechanisms of xylan biosynthesis in *Arabidopsis thaliana* (*Arabidopsis*). IRX9/IRX9L and IRX14/IRX14L from the GT43 family, and IRX10/IRX10L from GT47 are thought to be responsible for elongation of the xylan backbone (17-21). We have recently identified and characterized a loss of function mutation in the rice IRX10 homolog and shown that OsIRX10 is important for xylan deposition in vascular tissues of the stem (22). IRX7 (FRA8)/IRX7L (F8H) (from GT47), IRX8 (from GT8), and PARVUS (from GT8) may be responsible for synthesizing the oligosaccharide found at the reducing end of some dicot and conifer xylans (4, 18, 23, 24). GUX1 and GUX2 (from GT8) are thought to be responsible for adding both glucuronic acid and 4-O-methylglucuronic acid branches to xylan in *Arabidopsis* (25, 26). Recently, rice and wheat GT61 family genes were found to be responsible for α-(1, 3)-arabinosyl substitution on xylan (27). Thus far, the enzymes that add β-(1,2)-xylose to xylan have not been identified.

BRIEF SUMMARY OF THE INVENTION

Xylans have a β-1,4-linked xylose backbone with substitutions that include α-(1→2)-linked glucuronosyl, 4-O-methyl glucuronosyl, and α-1,2- and α-1,3-arabinofuranosyl residues. The substitutions are structurally diverse and vary by taxonomy, with grass xylan representing a unique composition from dicots and other monocots. To date, no enzyme has yet been identified that is specific to grass xylan synthesis.

This invention is based, in part, on the discovery that a rice GT61 family protein possesses β-1,2-xylosyl transferase activity, transferring xylose from UDP-xylose onto xylan. This mutant has been named XAX1 for Xylosyl Arabinosyl substitution of Xylan 1. Mutant XAX1 rice plants have a dwarfed phenotype and the leaves are deficient in xylose, ferulic acid, and coumaric acid, and have improved saccharification efficiency. We identified a xylose-deficient loss-of-function rice mutant in Os02g22380, a putative glycosyltransferase in a grass-specific subfamily of family GT61. Enzymatic fingerprinting of cell wall polysaccharides showed the specific absence in the mutant of a peak consisting of β-Xyl-α-Ara-(β-1,4-Xyl)$_4$. Rice XAX1 mutant plants are deficient in ferulic and coumaric acid, aromatic compounds that are attached to arabinose residues in xylan substituted with xylose. The XAX1 mutant plants exhibit an increased extractability of xylan and increased saccharification, probably reflecting a lower degree of diferulic cross-links. Activity assays with microsomes isolated from tobacco plants transiently expressing XAX1 demonstrated xylosyltransferase activity onto endogenous xylan acceptors. Our results provide insight into how substitutions may be modified for increased saccharification for biofuel generation.

The invention provides, in part, grass plants that have been engineered to inhibit endogenous expression of an XAX1 gene, methods of engineering such plants and methods of using the engineered plants, e.g., to obtain an increased amount of soluble sugar for biofuel production. In some embodiments, a polynucleotide encoding an exogenous XAX1 gene is introduced into the engineered plant to provide for expression of XAX1 in a particulard tissue, such as vessels. Accordingly, an exogenous XAX1 gene introduced into the plants is operably linked to a tissue-specific promoter, such as a vessel promoter.

In one aspect, the invention provides a grass plant in which an endogenous XAX1 gene is functionally disrupted, e.g., by inhibiting expression of the gene or otherwise mutagenizing the gene to inactivate or reduce expression, e.g., to less than 80% of the level of expression, typically less than 50% of the level of expression, more typically to less than 20%, or less than 10% of the level of expression in a corresponding wildtype grass plant in which the XAX1 gene is not functionally disrupted. In some embodiments, the promoter of the XAX1 gene is disrupted, e.g., by mutagenesis, so that XAX1 expression is reduced, e.g., to less than 80%, less than 70%, or less than 60% of the level of expression, typically less than 50% of the level of expression, more typically to less than 20%, or less than 10% of the level of expression in a corresponding wildtype grass plant in which the promoter of the XAX1 gene is not functionally disrupted.

In a further aspect, the invention provides a grass plant that comprises a recombinant expression cassette that encodes a polynucleotide that hybridizes to a XAX1 gene and inhibits expression of the XAX1 gene. In one embodiment, the plant comprises a recombinant expression vector that encodes a polynucleotide, wherein the polynucleotide is at least 50% or 60% identical, at least 65%, at least 70%, at least 75%, at least 80%, at least 85%, at least 90%, or at least 95% identical, to at least 100 or at least 200 contiguous nucleotides of a nucleic acid sequence of SEQ ID NO:1 or SEQ ID NO:3; or is at least 60% identical, at least 65%, at least 70%, at least 75%, at least 80%, at least 85%, at least 90%, or at least 95% identical, to at least 100 or at least 200 contiguous nucleotides of a nucleic acid sequence encoding SEQ ID NO:2, or a complement of such a nucleic acid. In some embodiments, the grass plant further comprises an exogenous XAX1 gene operably linked to a tissue-specific promoter, such as a vessel promoter. In some embodiments, the polynucleotide encoding the exogenous gene encodes a polypeptide having at least 45% identity, or at least 50%, at least 55%, at least 60%, at least 65%, at least 70%, at least 75%, at least 80%, at least 85%, at least 90%, or at least 95% to the amino acid sequence of SEQ ID NO:2. In some embodiments, the vessel-specific promoter is a VND6 or VND7 promoter.

In some embodiments, the polynucleotide comprises a sequence that is at least 90% identical to 20 contiguous nucleotides, or at least 30, 40, 50, 100, or at least 200 contiguous nucleotides, of a nucleic acid sequence of SEQ ID NO:1 or SEQ ID NO:3, or a complement thereof; or is at least 90% identical to 20 contiguous nucleotides, or at least 30, at least 40, at least 50, at least 100, or at least 200 contiguous nucleotides to a nucleic acid sequence encoding SEQ ID NO:2, or a complement of such a nucleic acid. In some embodiments, the polynucleotide encodes an siRNA, an antisense polynucleotide, a microRNA, or a sense suppression nucleic acid.

In some embodiments, a grass plant of the invention has at least a 10% reduction of hydroxycinnamate esters compared to a control plant that has not been genetically modified to reduce expression of an endogenous XAX1 gene.

In some embodiments, the grass plant has at least a 10% increase, and in some embodiments, at least a 20% or at least a 50% or more, in sugar extractability compared to a control grass plant that has not been genetically modified to reduce XAX1 gene expression. Grass plants that can be engineered in accordance with the invention, include, but are not limited to, rice, wheat, oats, rye, barley, corn, sorghum, millet, Miscanthus, sugarcane, bamboo, turfgrass, Brachypodium, switchgrass, hemp, meadow-grass, bluestem grass, bromegrass, *Festuca*, ryegrass, and bentgrass.

In some embodiments, the invention provides a plant cell from a plant that is engineered to inhibit endogenous expression of a XAX1 gene. In some embodiments, the invention provides a leaf, stem, stalk, or other part of a grass plant.

In another aspect, the invention provides a method of improving the amount of soluble sugar obtained from grass plant biomass material, the method comprising providing plant biomass material from any grass plant as described herein above that has decreased XAX1 expression; performing a saccharification reaction; and obtaining soluble sugar. In some embodiments, the XAX1 gene is deleted or knocked out in the plant. In some embodiments, the grass plant comprises a recombinant expression vector that encodes a nucleic acid that inhibits XAX1 gene expression. In some embodiments, the amount of sugar extractable from the plant biomass material is increased by at least 10%, or at least 20%, or at least 50%, or more, compared to the amount of sugar extractable from plant biomass material from the wild-type grass plant.

In yet another aspect, the invention provides a saccharification reaction comprising plant biomass material from such engineered grass plants.

In a further aspect, the invention provides a method of obtaining an increased amount of soluble sugars from a grass plant in a saccharification reaction, the method comprising inhibiting the expression of an endogenous XAX1 gene in the plant, using plant material in a saccharification reaction, thereby increasing the amount of extracted sugar compared to the wild-type grass plant in which expression of the endogenous gene has not been inhibited.

In some embodiments, the inhibiting step comprises introducing into the grass plant an expression cassette that encodes a polynucleotide that hybridizes to an endogenous XAX1 gene and inhibits expression In some embodiments, the polynucleotide is at least 70% identical to at least 100 or at least 200 contiguous nucleotides of a nucleic acid sequence of SEQ ID NO:1, or a complement thereof, or is at least 70% identical to at least 100 or at least 200 contiguous nucleotides of a nucleic acid sequence encoding SEQ ID NO:2, or a complement of such a nucleic acid. In some embodiments, the polynucleotide comprises a sequence that is at least 90% identical to at least 50, or at least 100, or at least 200 contiguous nucleotides to a nucleic acid sequence of SEQ ID NO:1 or a complement thereof; or is at least 90% identical to at least 50, or at least 100, or at least 200 contiguous nucleotides of a nucleic acid sequence encoding SEQ ID NO:2 or a complement of such a nucleic acid. In some embodiments, the polynucleotide encodes an siRNA, an antisense polynucleotide, a microRNA, or a sense suppression nucleic acid.

In some embodiments, the grass plant that is used in accordance with this method is rice, wheat, oats, rye, barley, corn, sorghum, millet, Miscanthus, sugarcane, bamboo, turfgrass, Brachypodium, switchgrass, hemp, meadow-grass, bluestem grass, brome-grass, *Festuca*, ryegrass, or bentgrass.

In yet another aspect, the invention provides a method of improving the amount of soluble sugar obtained from plant biomass material, the method comprising providing a grass plant biomass material from a plant in which endogenous XAX1 gene expression is inhibited; performing a saccharification reaction; and obtaining soluble sugar. In some embodiments, the amount of sugar extractable from the plant biomass material is increased by at least 10% compared to the amount of sugar extractable from plant biomass material from the wild-type plant.

In another aspect, the invention provides bulk harvested material comprising material from a grass plant, or two or more grass plants, that have decreased expression of an endogenous XAX1 gene as described herein. In some embodiments, the grass plant is rice, wheat, oats, rye, barley, corn, sorghum, millet, Miscanthus, sugarcane, bamboo, turfgrass, Brachypodium, switchgrass, hemp, meadow-grass, bluestem grass, brome-grass, *Festuca*, ryegrass, and bentgrass.

In some embodiments, the invention provides forage material comprising material from a grass plant, or two or more grass plants of the invention that have been genetically modified to decrease expression of an endogenous XAX1 gene.

DETAILED DESCRIPTION OF THE INVENTION

Definitions

Figure 1:
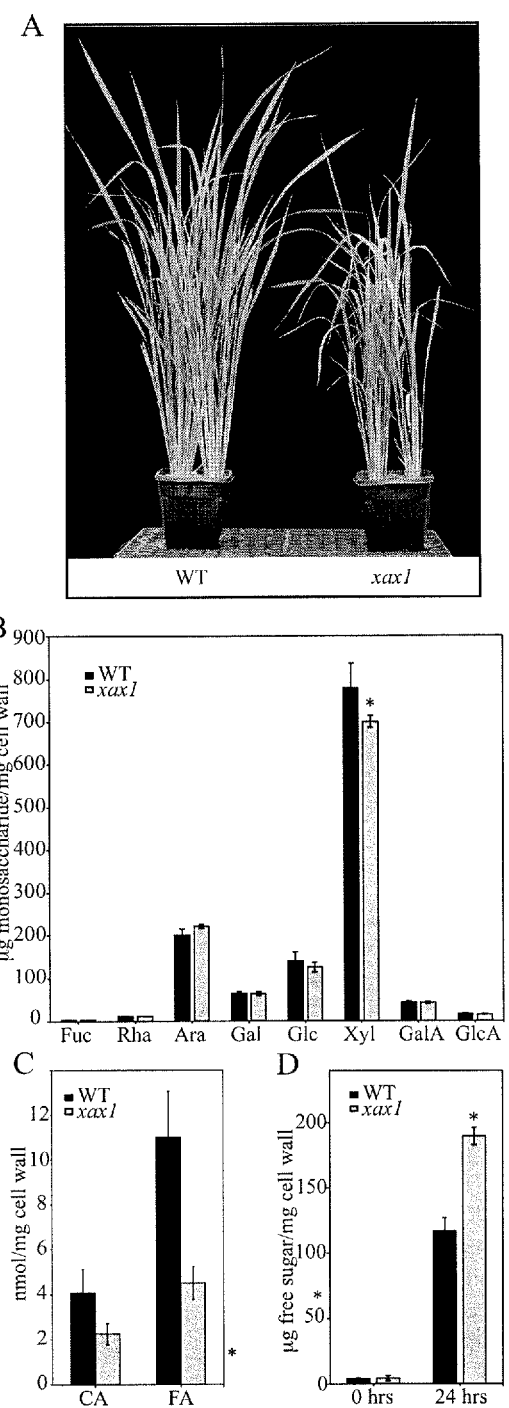
FIG. 1. XAX1 T-DNA insertional rice mutant. (A) Dwarfed phenotype of XAX1 plants at 5 weeks. (B) Monosaccharide composition of total plant cell wall after TFA hydrolysis, separated and quantified on the HPAEC. (C) Ferulic and p-coumaric acid amounts released upon base-hydrolysis of total cell wall preparations and acid-catalyzed depolymerization of carbohydrate-free residues. (D) Saccharification of cell wall after 120° C. pretreatment and cellulase and hemicellulase enzymatic digestion; quantified by DNS. Error bars represent SD with at least 3 biological reps.

The term "XAX1 gene," in the context of this invention, refers to a nucleic acid that encodes a grass-specific member of family GT6 that has xylosyltransferase activity. In some embodiments, an XAX1 gene or XAX1 nucleic acid comprises the nucleic acid sequence of SEQ ID NO:1 or SEQ ID NO:3 or a fragment thereof, or is substantially identical to SEQ ID NO:1 or SEQ ID NO:3 or a fragment thereof. Thus, a XAX1 gene can, for example, (1) have at least 70% identity, 75% identity, 80% identity, 85% identity, 90% identity, at least 95% or greater, identity to SEQ ID NO:1 or SEQ ID NO:3 or to a fragment thereof over a comparison window of at least 200, 250, 300, 350, 400, 450, or more nucleotides; or (2) comprise at least 200, 250, 300, 350, 400, 450, or more, contiguous nucleotides of SEQ ID NO:1 or SEQ ID NO:3. In some embodiments, an XAX1 gene encodes a polypeptide that has at least 45%, 50%, 55%, 60%, 65%, 70%, 75%, 80%, 85%, 90%, or 95%, or greater identity to SEQ ID NO:2. In some embodiments, an XAX1 gene encodes a polypeptide that has at least region 45%, 50%, 55%, 60%, 65%, 70%, 75%, 80%, 85%, 90%, or 95%, or greater identity to residues 605-780 of SEQ ID NO:2.

A "XAX1 polypeptide" is an amino acid sequence encoded by a XAX1 nucleic acid. In some embodiments, an XAX1 polypeptide comprises the amino acid sequence of SEQ ID NO:2, or is substantially identical to SEQ ID NO:2 or a fragment or domain thereof that has xylosytransferase activity.

As used herein, a "homolog" or "ortholog" of an XAX1 gene is a second gene in the same plant type or in a different plant type that is substantially identical (determined as described below) to a sequence in a first gene.

The terms "nucleic acid" and "polynucleotide" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The terms "decreased expression," "reduced expression," or "inhibited expression" of an endogenous XAX1 gene refer interchangeably to a reduction in the level of expression of the XAX1 gene in an engineered plant in which XAX1 gene expression has been disrupted compared to the level of expression in a wild-type plant in which XAX1 expression has not been disrupted. Thus, decreased expression can be a reduction in expression of an XAX1 gene of 10%, 20%, 30%, 40%, 50%, 60%, 70%, 80%, or 90% or greater. Decreased expression can be assessed by measuring decreases in the level of RNA encoded by the gene and/or decreases in the level of XAX1 protein or protein activity. XAX1 protein/protein activity can be assessed directly or indirectly, e.g., by measuring an endpoint such as amount of sugar extractable from a plant in which a XAX1 gene is inhibited, or by assessing levels of ferulic and/or coumaric acids in a plant in which a XAX1 gene is inhibited. Activity may also be assessed by measuring xylosyltransferase activity, for example using microsome from the plant to measure activity onto endogenous xylan acceptors.

In the context of this invention, the phrase "functionally inactive" with regard to an endogenous XAX1 gene means that the XAX1 gene is deleted or otherwise mutated or inhibited, such that expression of the gene does not occur, or occurs at a low level, e.g., at a level of less than 20% or less than 10% compared to a corresponding in plant in which the XAX1 gene is not deleted or otherwise mutated or inhibited.

The phrase "substantially identical," in the context of two nucleic acids or polypeptides, refers to a sequence or subsequence that has at least 50% identity, typically at least 60% sequence identity, to a reference sequence. Percent identity can be any integer from 50% to 100%. In some embodiments, a sequence is at least 60%, 65%, 70%, 75%, 80%, 85%, 90%, 91%, 92%, 93%, 94%, 95%, 96%, 97%, 98%, or 99% identical when compared to a reference sequence. For example, an XAX1 polypeptide may have a sequence that is at least 60%, 65%, 70%, 75%, 80%, 85%, 90%, 91%, 92%, 93%, 94%, 95%, 96%, 97%, 98%, or 99% identical to a sequence of SEQ ID NO:2.

In the case of inhibition of endogenous genes (e.g., by antisense, or sense suppression) one of skill will recognize that the introduced polynucleotide sequence need not be perfectly identical and may be "substantially identical" to a sequence of the gene from which it was derived. One of skill will also recognize that for inhibition of endogenous genes, the introduced sequence need not be perfectly identical to a sequence of the target endogenous gene. The introduced polynucleotide sequence will typically be at least substantially identical (as determined below) to the target endogenous sequence. Thus, an introduced "polynucleotide sequence from" an XAX1 gene may not be identical to the target XAX1 gene to be suppressed, but is functional in that it is capable of inhibiting expression of the target XAX1 gene.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. In some embodiments, percent identity is determined using the BLAST2 algorithm set at the default settings.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. A "comparison window" may be, e.g., 20, 50, 100, 400, or more nucleotides ore amino acids in length; or may be the entire length of the sequences being compared.

Proteins that are substantially identical include those that have conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "recombinant," when used in reference to, e.g., a cell or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "endogenous" in the context of this invention refers to a gene or protein that is originally present in a naturally occurring grass plant. Conversely, an "exogenous" gene or protein is one that originates outside the grass plant. This may be a gene or protein from another species, but also refers to a gene or protein that is from the same species, but that is encoded by a recombinant construct that is introduced into the plant.

The term "expression vector" refers to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "biomass," as used herein, refers to plant material that is processed to provide a product, e.g., a biofuel such as ethanol, or livestock feed. Such plant material can include whole plants, or parts of plants, e.g., stems, leaves, branches, shoots, roots, tubers, and the like.

The term "plant," as used herein, refers to whole plants, shoot vegetative organs and/or structures (e.g., leaves or stems), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like). The term also encompasses individual plant cells, groups of plant cells (e.g., cultured plant cells), protoplasts, plant extracts, seeds, and progeny thereof. The term includes plants of a variety of a ploidy levels, including polyploid, diploid and haploid.

The term "progeny" refers generally to the offspring of a cross, and includes direct F1 progeny, as well as later generations of F2, F3, etc.

The terms "saccharification" or "saccharification reaction" refer to a process of converting biomass, usually cellulosic or lignocellulosic biomass, into monomeric sugars, such as glucose and xylose. "Soluble sugar" refers to the monomeric sugar that is produced from the saccharification of biomass.

The term "improving the amount" or "improved amount," when referring to an amount of sugar or soluble sugar obtained from a plant of the present invention, refers to an increase in the amount or yield of sugar that is obtained from saccharification of biomass per amount of starting material, in comparison to corresponding biomass from a wild-type plant. In the context of the present invention, "corresponding biomass from a wild-type plant" refers to plant material that is from the same part of the plant as the biomass from a plant having inhibited expression of an endogenous XAX1 gene. As understood in the art, improved amount or improved yield is based upon comparisons of the same amount of corresponding plant material. As used herein, "increasing sugar extractability" refers to the ability to increase the yield of sugar from saccharification of biomass per amount of starting material.

The term "bulk harvested material" refers to combined plant material harvested from at least two plants, preferably at least 5, 10, 25, 50, 100, 500, or 1000 or more plants. The plant material may be whole plants, or parts of the plants, e.g., leaves or stems harvested from the plants. In some embodiments, the plant material present in the bulk harvested material is crushed or milled to a desired particle size, e.g., a size that is useful for producing biofuel.

INTRODUCTION

This invention is based, in part, on the discovery that a putative glycosyltransferase in a grass-specific subfamily of family GT6, is a xylosyltransferase, XAX1, and that the inhibition of the gene XAX1 in grass plants results in decreased levels of xylose, ferulic acid, and coumaric acid compared to wildtype plants and in improved saccharification efficiency, an important trait for the production of cellulosic biofuels.

In some embodiments, endogenous XAX1 expression is inhibited in some tissues of a grass plant, e.g., in nonvascular tissues, but expression of an XAX1 polypeptide is maintained in other tissues, e.g., vascular tissues by providing an exogenous XAX1 gene that is expressed in a tissue-specific manner. This provides for a plant that is suitable for biomass energy, and the plant, or biomass material (e.g., stems, leaves, branches, shoots, roots, tubers, and the like) or bulk harvested material from the plant is used in a saccharification reaction to obtain an increased amount of soluble sugar, which can, e.g., be used for biofuel production.

The present invention also provides methods of obtaining an increased amount of soluble sugars from a plant, or from biomass material or bulk harvested material from the plant, by inhibiting endogenous XAX1 expression in the plant. In some embodiments, the amount of soluble sugar that can be extracted from the plant is at least 10% more than what can be extracted from a wild-type plant in which XAX1 expression has not been inhibited.

In some embodiments, e.g., where inhibiting endogenous XAX1 expression results in decreased growth relative to a wildtype plant, a plant can be additionally modified to express an exogenous XAX1 gene in a desired tissue, such as vessels. A plant in which endogenous XAX1 expression is inhibited can also be further bred, e.g., back-crossed, for a desired property such as improved growth.

Plants in which XAX1 Expression can be Inhibited

The expression of XAX1 expression can be inhibited as described herein in various kinds of grass plants, including, but not limited rice, wheat, oats, rye, barley, corn, sorghum, millet, miscanthus, sugarcane, bamboo, turfgrass, brachypodium, switchgrass, hemp, meadow-grass, bluestem grass, brome-grass, festuca, ryegrass, and bentgrass.

Inhibition of XAX1 Expression

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel et al., eds., 1994-1999, updated through 2008).

A. XAX1 Nucleic Acids and Proteins

XAX1 is a member of a grass-specific subfamily of GT61 proteins. An example of a rice XAX1 protein sequence is provided in SEQ ID NO:2. The sequence is closely related to protein sequences in sorghum (e.g., SEQ ID NOS:5 and 8) and Brachypodium (e.g., SEQ ID NOS:4, 6, and 7), For example, the rice XAX1 amino acid sequence SEQ ID NO:2 has 82% identity to SEQ ID NO:6 (Bradi3g11340.1); 78% identity to SEQ ID NO:7 (Bradi1g06560.1) 74% identity to SEQ ID NO:8 (Sb04g000840.1); 70% identity to SEQ ID NO:4 (Bradi4g27360.1); 69% to SEQ ID NO:5 (Sb10g018270.1). SEQ ID NO:2 also has 63% identity to the protein encoded by Sb03g008020.1; 62% identity to the protein encoded by Bradi2g01380.1, 54% identity to the protein encoded by Os12g13640.1, and 51% identity to the protein encoded by Sb03g008010.1_(S.bicolor).

An XAX1 nucleic acid that is targeted for inhibition in the present invention encodes a protein that is substantially identical to SEQ ID NO:2. "Substantially identical," as used herein, refers to a sequence or subsequence that has at least 45% or 50% identity, typically at least 60% sequence identity or at least 70% sequence identity or higher, to a reference sequence.

Thus, in some embodiments, a XAX1 nucleic acid that is targeted for inhibition in the present invention encodes a polypeptide comprising a sequence that is at least 70% identical or at least 75%, 80%, 85%, 90%, 91%, 92%, 93%, 94%, 95%, 96%, 97%, 98%, or at least 99% identical to an amino acid of SEQ ID NO:2, or a fragment thereof. In some embodiments, a XAX1 nucleic acid that is targeted for inhibition is at least 70% identical, at least 75%, 80%, 85%, 90%, 91%, 92%, 93%, 94%, 95%, 96%, 97%, 98%, or 99% identical to at least 100 contiguous nucleotides, or at least 200 contiguous nucleotides, of a nucleic acid sequence encoding SEQ ID NO:2.

In some embodiments, a XAX1 nucleic acid that is targeted for inhibition in the present invention comprises a sequence having at least 70%, at least 75%, 80%, 85%, 90%, 91%, 92%, 93%, 94%, 95%, 96%, 97%, 98%, or 99% identical to a nucleic acid sequence of SEQ ID NOs:1 or 3, or a fragment thereof. In some embodiments, a XAX1 nucleic acid that is targeted for inhibition is at least 70% identical, at least 75%, 80%, 85%, 90%, 91%, 92%, 93%, 94%, 95%, 96%, 97%, 98%, or 99% identical to at least 200 contiguous nucleotides of a nucleic acid sequence of SEQ ID NO:1 or SEQ ID NO:3.

B. Methods of Inhibiting XAX1 Expression

The invention provides methods of improving the amount of soluble sugar extractable from a grass plant, grass plant biomass material, or bulk harvested material from a grass plant by inhibiting expression of a nucleic acid molecule encoding XAX1. Endogenous expression of the XAX1 gene can be inhibited using any number of techniques well known in the art, such as antisense, siRNA, microRNA, dsRNA, sense suppression, mutagenesis, or use of a dominant negative inhibition strategy. In some embodiments, the level of expression of the protein is reduced.

In some embodiments, XAX1 expression is inhibited by an antisense polynucleotide. In antisense technology, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of a XAX1-encoding sequence can be useful for producing a plant in which XAX1 expression is suppressed. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. In some embodiments, a sequence of at least, e.g., 20, 25, 30, 50, 100, 200, or more continuous nucleotides (up to mRNA full length) substantially identical to an endogenous XAX1 mRNA, or a complement thereof, can be used.

Catalytic RNA molecules or ribozymes can also be used to inhibit expression of a XAX1 gene. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum* nodiflorum mottle virus and subterranean clover mottle virus. The design and use of target RNA-specific ribozymes is described in Haseloff et al. *Nature,* 334:585-591 (1988).

Another method by which XAX1 expression can be inhibited is by sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity can exert a more effective repression of expression of the endogenous sequences. In some embodiments, sequences with substantially greater identity are used, e.g., at least about 80, at least about 95%, or 100% identity are used. As with antisense regulation, further discussed below, the effect can be designed and tested to apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. Furthermore, the introduced sequence need not have the same intron or exon pattern, and identity of non-coding segments will be equally effective. In some embodiments, a sequence of the size ranges noted above for antisense regulation is used, i.e., 30-40, or at least about 20, 50, 100, 200, 500 or more nucleotides.

Endogenous gene expression may also be suppressed by means of RNA interference (RNAi) (and indeed co-suppression can be considered a type of RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct Genom* 5: 240-244 (2004); Lu, et al., *Nucleic Acids Res.* 32(21):e171 (2004)).

Thus, in some embodiments, inhibition of a XAX1 gene is accomplished using RNAi techniques. For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting plants may then be screened for a phenotype associated with the target protein, for example, screening for an increase in the extractability of sugar from the plants as compared to wild-type plants, and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases. Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and *Fire Nature* 395: 854 (1998).

Yet another way to suppress expression of an endogenous plant gene is by recombinant expression of a microRNA that suppresses a target (e.g., a XAX1 gene). Artificial microRNAs are single-stranded RNAs (e.g., between 18-25-mers, generally 21-mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

Another example of a method to reduce levels of GALS employs riboswitch techniques (see, e.g., U.S. Patent Application Publication Nos. US20100286082, and US20110245326).

In a further embodiment, a tissue-specific promoter that directs expression of a nuclease (zinc-finger or TALEN) that can be engineered to recognize a target XAX1 gene sequence can be used to inhibit XAX1 expression in a tissue of interest).

One of skill in the art will recognize that using technology based on specific nucleotide sequences (e.g., antisense or sense suppression, siRNA, microRNA technology, etc.), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Alternatively, random mutagenesis approaches may be used to disrupt or "knock-out" the expression of a XAX1 gene using either chemical or insertional mutagenesis, or irradiation. One method of mutagenesis and mutant identification is known as TILLING (for targeting induced local lesions in genomes). In this method, mutations are induced in the seed of a plant of interest, for example, using EMS treatment. The resulting plants are grown and self-fertilized, and the progeny are assessed. For example, the plants may be assed using PCR to identify whether a mutated plant has a XAX1 mutation, e.g., that reduces expression of a XAX1 gene, or by evaluating whether the plant has reduced levels of phenolics or increased sugar extractability, or decreased lignin content in a part of the plant that expressed the XAX1 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

The invention also provides "knockout XAX1 plants" where mutagenesis, e.g., disruption of a XAX1 gene sequence by, e.g., homologous recombination, leads to loss of expression of the endogenous gene. Methods of generating "knockout" plants are well-known in the art, see, e.g., Strepp (1998) Proc Natl. Acad. Sci. USA 95:4368-4373; Miao (1995) Plant J7:359-365. See discussion on transgenic plants, below.

Another method for abolishing or decreasing the expression of a XAX1 gene is by insertion mutagenesis using the T-DNA of *Agrobacterium tumefaciens*. After generating the insertion mutants, the mutants can be screened to identify those containing the insertion in a XAX1 gene. Mutants containing a single mutation event at the desired gene may be crossed to generate homozygous plants for the mutation (Koncz et al. (1992) Methods in *Arabidopsis* Research. World Scientific).

Another method to disrupt a XAX1 gene is by use of the cre-lox system (for example, as described in U.S. Pat. No. 5,658,772).

In further embodiments, XAX1 gene expression can be disrupted by targeting a promoter that controls expression of the endogenous XAX1 gene. The promoter is 5' to the transcription start site and typically includes from 250-500, or to 1000 or to 1500 base pairs upstream of the transcription start site.

Expression of XAX1 Gene Inhibitors

To use isolated sequences in the above techniques, recombinant expression vectors suitable for transformation of plant cells such as grass plant cells are prepared. For example, a polynucleotide sequence encoding a sequence that inhibits expression of an endogenous XAX1 gene (described in further detail herein) can be combined with other regulatory sequences which will direct the expression of the inhibitory polynucleotide sequence in the intended cells, e.g., rice or other grass plant cells. Typically, plant transformation vectors include one or more cloned plant coding sequences (genomic or cDNA) under the transcriptional control of 5' and 3' regulatory sequences and a dominant selectable marker. Such plant transformation vectors typically contain a promoter (e.g., a regulatory region controlling inducible or constitutive, environmentally-or developmentally-regulated, or cell- or tissue-specific expression).

In some embodiments, a constitutive plant promoter may be used for directing expression of the polynucleotide in all tissues of the plant. Examples of constitutive plant promoters include: the cauliflower mosaic virus (CaMV) 35S promoter, which confers constitutive, high-level expression in most plant tissues (see, e.g., Odel et al., (1985) Nature 313:810); the nopaline synthase promoter (An et al., (1988) Plant Physiol. 88:547); and the octopine synthase promoter (Fromm et al., (1989) Plant Cell 1:977). Additional constitutive regulatory elements, including those for efficient expression in monocots, also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)).

Alternatively, a plant promoter may direct expression of the polynucleotide of the invention in a specific tissue (tissue-specific promoters). For example, in some embodiments, it is desirable to inhibit expression in non-vascular tissues. Tissue-specific promoters are transcriptional control elements that are only active in particular cells or tissues at specific times during plant development, such as in vegetative tissues or reproductive tissues. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Alternatively, the plant promoter may be under more precise environmental control (inducible promoters). Examples of environmental conditions that may affect transcription by inducible promoters include anaerobic conditions, elevated temperature, drought, or the presence of light. Examples of environmental promoters include drought-inducible promoter of maize (Busk (1997) supra); the cold, drought, and high salt inducible promoter from potato (Kirch (1997) *Plant Mol. Biol.* 33:897 909). Plant promoters that are inducible upon exposure to plant hormones, such as auxins, may also be employed. For example, the invention can use the auxin response elements E1 promoter fragment (AuxREs) in the soybean (*Glycine max* L.) (Liu (1997) *Plant Physiol.* 115:397 407); the auxin-responsive *Arabidopsis* GST6 promoter (also responsive to salicylic acid and hydrogen peroxide) (Chen (1996) *Plant J.* 10: 955 966); the auxin-inducible parC promoter from tobacco (Sakai (1996) 37:906 913); a plant biotin response element (Streit (1997) *Mol. Plant. Microbe Interact.* 10:933 937); and, the promoter responsive to the stress hormone abscisic acid (Sheen (1996) *Science* 274:1900 1902).

Plant promoters which are inducible upon exposure to chemical reagents that can be applied to the plant, such as herbicides or antibiotics, may also be used in vectors as described herein. For example, the maize In2 2 promoter, activated by benzenesulfonamide herbicide safeners, can be used; application of different herbicide safeners induces distinct gene expression patterns, including expression in the root, hydathodes, and the shoot apical meristem. Other promoters, e.g., a tetracycline inducible promoter; a salicylic acid responsive element promoter, promoters comprising copper-inducible regulatory elements; promoters comprising ecdysone inducible regulatory elements; heat shock inducible promoters, a nitrate-inducible promoter, or a light-inducible promoter may also be used.

Plant expression vectors may also include RNA processing signals that may be positioned within, upstream or downstream of the inhibitory sequence.

Plant expression vectors routinely also include dominant selectable marker genes to allow for the ready selection of transformants. Such genes include those encoding antibiotic resistance genes (e.g., resistance to hygromycin, kanamycin, bleomycin, G418, streptomycin or spectinomycin), herbicide resistance genes (e.g., phosphinothricin acetyltransferase), and genes encoding positive selection enzymes (e.g. mannose isomerase).

Once an expression cassette comprising a polynucleotide encoding an inhibitor of the expression of a XAX1 gene has been constructed, standard techniques may be used to introduce the polynucleotide into a plant in order to modify XAX1 activity and accordingly, the synthesis of phenolics in the plant or plant part in which the XAX1 target nucleic acid is expressed. See protocols described in Ammirato et al. (1984) Handbook of Plant Cell Culture—Crop Species. Macmillan Publ. Co. Shimamoto et al. (1989) Nature 338: 274-276; Fromm et al. (1990) Bio/Technology 8:833-839; and Vasil et al. (1990) Bio/Technology 8:429-434.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants or the ability to grow on a specific substrate, and selection of transformants can be accomplished by exposing the plants to appropriate concentrations of the antibiotic, herbicide, or substrate.

XAX1 nucleic acids can be obtained using many methods known in the art. Such methods can involve amplification reactions such as PCR and other hybridization-based reactions or can be directly synthesized.

In some embodiments, a grass plant in which XAX1 expression is decreased in accordance with the invention, may be further modified to express an exogenous XAX1 in a desired tissue, such as vessel, or to express exogenous XAX1 under desired environmental conditions. Vectors for expressing exogenous XAX1 can be generated using techniques well known in the art. Various regulatory components are described above. In the present invention, a polynucleotide that expresses an exogenous XAX1 typically encodes a polypeptide having at least 50% identity, more typically at least 60%, 65%, 70%, 75%, 80%, 85%, 90%, 95%, or greater, identity to SEQ ID NO:2.

Expression of a polynucleotide encoding a XAX1 protein in a desired tissue can be achieved using a tissue-specific promoter, such as a promoter described above. Thus, for example, the XAX1 polynucleotide may be introduced into a plant such that expression is controlled by a vessel-specific promoter, e.g., a VND6 or VND7 promoter. (See, e.g., PCT/US2012/023182 for illustrative promoter sequences). Other examples of tissue-specific promoters include promoters that initiate transcription primarily in certain tissues, such as vegetative tissues, e.g., roots or leaves. Other examples are promoters that direct expression specifically to cells and tissues with secondary cell wall deposition, such as xylem and fibers. Examples of tissue-specific include promoters for IRX1, IRX3, IRX5, IRX8, IRX9, IRX14, IRX7, IRX10, GAUT13, or GAUT14 genes.

Screening for Plants Having Suppressed XAX1 Expression

After transformed plants are selected, parts of the plants may be evaluated to determine the level of XAX1 gene expression in a part of the plant that expresses the XAX1 gene, e.g., by evaluating the level of RNA or protein, by determining the amounts of soluble sugars that can be extracted from the plants, or by evaluating the levels of other compounds, such as ferulate and coumarate esters. These analyses can be performed using any number of methods known in the art.

In some embodiments, the amount of soluble sugar that can be extracted from a plant can be measured by a saccharification reaction, e.g., enzymatic saccharification. Methods of enzymatic saccharification are known in the art. Briefly, plants or plant biomass material (e.g., leaves and stems) are pre-treated with hot water or dilute acid, followed by enzymatic saccharification using a mixture of cellulose and beta-glucosidase in buffer and incubation of the plants or plant biomass material with the enzymatic mixture. Following incubation, the yield of the saccharification reaction can be readily determined by measuring the amount of reducing sugar released, using a standard method for sugar detection, e.g. the dinitrosalicylic acid method well known to those skilled in the art. Plants engineered in accordance with the invention provide a higher sugar yield.

Alternatively, the level of XAX1 gene expression can be assessed by measuring the of a plant; or the ferulate and/or coumarate ester content of xylan in the plant. Methods of performing such analyses are known in the art (see, e.g., the EXAMPLES section; and e.g., Harholt, et al., *Plant Biotechnology* Journal 8:351-362, 2010).

Plants of the invention that exhibit reduced XAX1 gene expression have at least a 5% increase in sugar obtained from a reaction, e.g., as assessed by a saccharification reaction, typically at least 10% increase in sugar extractability, or more often at least 15%, 20%, 30%, 40%, or 50% or more increase in sugar compared to a plant that has not been engineered to decrease expression of the XAX1 gene. As understood in the art, XAX1-mediated increase in sugar extractability may occur in one or more parts of the plants, e.g., sugar extractability may be increased in a leaf and/or a stem.

Plants of the invention that exhibit reduced XAX1 gene expression can also have a lignin content that is reduced by at least 10%, often by at least 15%, at least 20%, at least 30%, at least 40%, or at least 50% compared to a plant that has not been engineered to decrease expression of the XAX1 gene. As understood in the art, XAX1-mediated decrease in lignin content may occur in one or more parts of the plants, e.g., lignin content may be decreased in the stem.

Plants, plant biomass material, or bulk harvested material from grass plants that are genetically modified to reduce expression of an endogenous XAX1 gene can be used in a variety of reactions, including fermentation reactions. Such reactions are well known in the art. For example, fermentation reactions such as yeast or bacterial fermentation reactions may employ plants of the present invention to obtain ethanol, butanol, lipids, and the like. For example, the plants may be used in industrial bioprocessing reactions that include fermentative bacteria, yeast, or filamentous fungi.

Plants, plant biomass material, or bulk harvested material from grass plants that are genetically modified to reduce expression of an endogenous XAX1 gene can be used as forage material for an animal to improve digestion in vivo. In some embodiments, the invention provides animal feed comprising grass plant biomass from a plant of the invention. In some embodiments, the invention provides a fiber fraction obtained from plant material from a plant of the invention. Such a fiber fraction may be used, for example, in food materials for animals, including humans.

In some embodiments, plants in which XAX1 expression is suppressed, have undesirable properties, such as decreased growth relative to a wildtype plant. As understood in the art, one of skill can use standard plant breeding techniques, such as back-crossing, to improve a desired characteristic of XAX1-deficient plants.

EXAMPLES

Example 1: Identification and Characterization of an XAX1 Mutant

XAX1 is a Previously Uncharacterized Xylan Biosynthesis Gene in Rice

Figure 6:
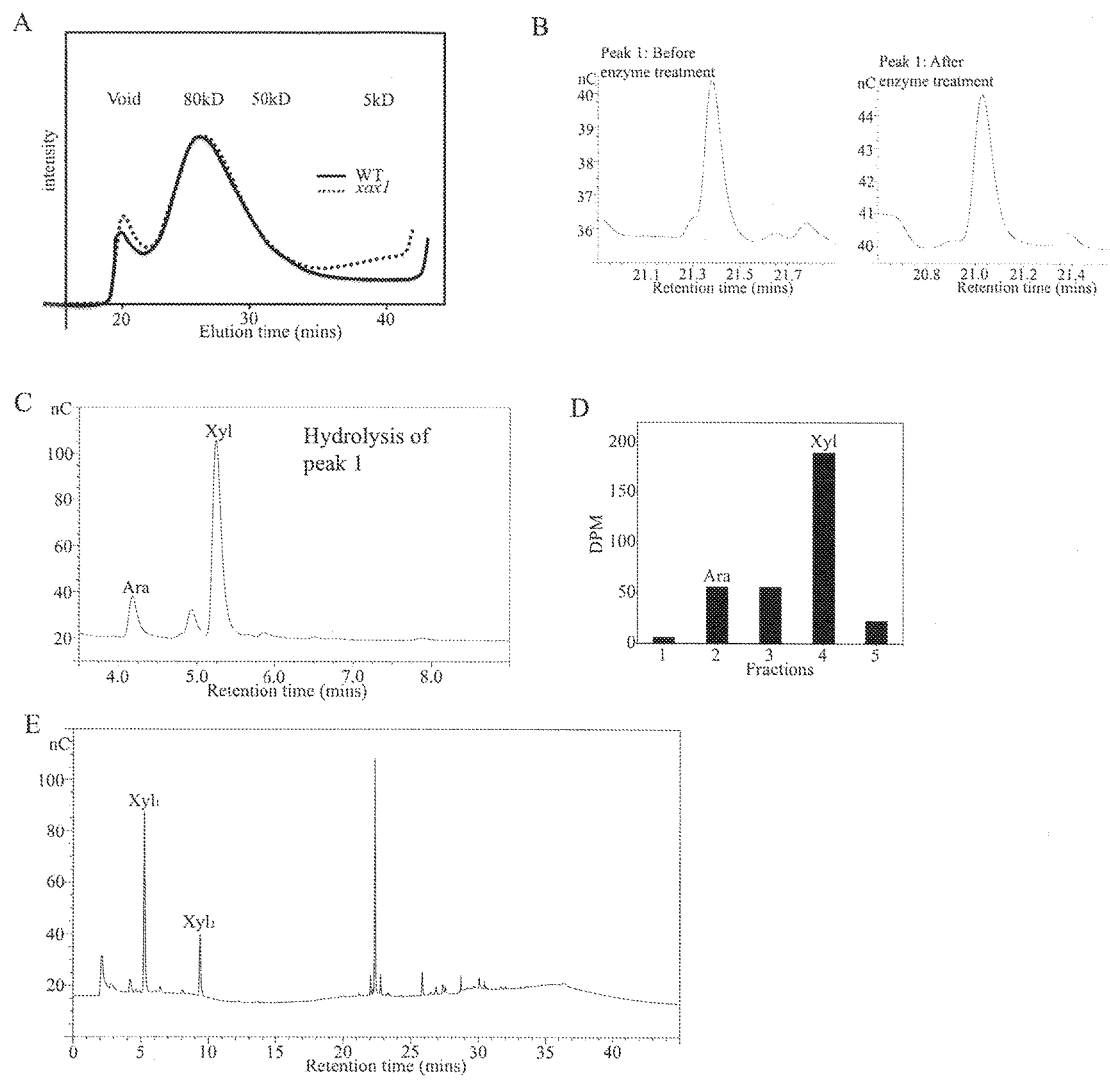
FIG. 6. Xylan composition analysis. (A) Size-exclusion chromatography (SEC) profiles of wild-type and mutant. Fractions soluble in 1 M KOH were analyzed by SEC using a Superose 12 column. The elution times of dextran molecular markers are indicated. Three biological replicates of both WT and mutant were analyzed and only insignificant differences could be observed. (B) HPAEC profile of arabinofuranosidase treatment of isolated peak 1 from wild type rice showing no shift in retention time consistent with no arabinose release indicating that 'peak 1' has no terminal arabinose. (C) HPAEC profile of TFA hydrolysis of isolated peak 1 from wild type rice showing xylose and arabinose peaks. (D) Analysis of endogenous products after UDP-[$^{14}$C]Xylose incubation with microsomes. TFA hydrolyzed product of activity assay (FIG. 3C), run on a TLC plate to separate sugars. Fraction 2 is where Arabinose runs and fraction 4 is where xylose runs. Less than 22% of the counts are in the arabinose fraction, indicating that the epimerase activity is minimal. (E) HPAEC profile of Xylan fingerprinting of *Selaginella* leaves after xylanase treatment showing lack of peaks that contain arabinose (as seen in FIG. 2A).

We identified a mutant with a mutation in the third exon that knocked out Os02g22380, a gene member that is part of a grass specific clade in the GT61 family. We identified this gene as a putative xylosyltransferase, based on its dwarfed phenotype and xylose deficiency in cell wall alcohol insoluble residue (AIR) in young rice leaves (FIGS. 1A and B). While the majority of all xylose in rice is derived from xylan, we confirmed that the deficiency was seen in the hemicellulose fraction (1M KOH) of sequentially extracted cell wall material (FIG. 6). Based on this biochemical phenotype and subsequent data described below, we named the mutant Xylosyl Arabinosyl substitution of Xylan 1 (XAX1).

Figure 2:
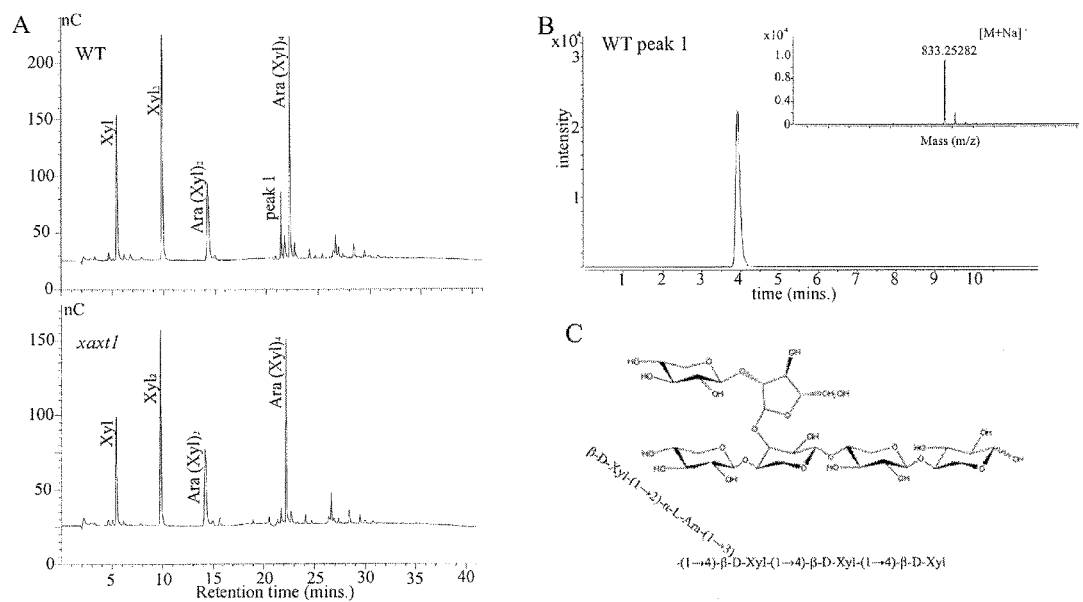
FIG. 2. Xylan fingerprinting and characterization of oligomer lacking in mutant. (A) HPAEC profiles of oligosaccharides released after endoxylanase treatment of xylan, showing peak 1 not found in mutant plants. Profile consistent between three biological replicates. (B) LC-MS of isolated peak 1 fraction from wild type rice. (C) Proposed structure of peak 1 lacking in XAX1 mutant plants consistent with mass and insensitivity to arabinofurosidase.

To gain further insight into the nature of the xylose deficiency, AIR was subjected to mild TFA hydrolysis, which preferentially cleaves arabinofuranosyl residues from the xylan backbone. A comparison of mild versus complete hydrolysis of AIR showed a stronger decrease in xylose (7.0%) than with total hydrolysis (2.6%), which indicates that the xylose deficiency is a substitution rather than a xylan chain deficiency (FIGS. 5 A and B)). Extraction of saponified AIR revealed a strong decrease in both ferulic acid (59%) and coumaric acid (44%) (FIG. 1C), aromatic compounds known to be attached to arabinose residues in xylan that are substituted with xylose (12). The 4M KOH cell wall fraction of AIR was further characterized by enzymatic fingerprinting with M6 endoxylanase (30). The released oligosaccharides were separated and quantified by high performance anion exchange chromatography with electrochemical detection (HPAEC-PAD) (FIG. 2A). Notably, XAX1 showed an absence of one peak eluting at about 22 min while the four other major peaks were found in both wild type and mutant. The unknown 'peak 1' was isolated from the wild type and determined by mass spectrometry to be a hexaose composed of pentose sugars (i.e. Xyl and Ara) (FIG. 2B). Unlike the peaks identified as AraXyl2 and AraXyl4, 'peak 1' was not modified with α-arabinofuranosidase treatment (FIG. 6B), an enzyme that hydrolyzes terminal α-arabinofuranose linkages (31) indicating that the peak lacked terminal α-arabinofuranose residues, even though it contained arabinose based on total hydrolysis of the isolated peak (FIG. 6C). It was concluded from this analysis that 'peak 1' was the oligomer: β-Xyl-α-Ara(β-1, 4-Xyl)4 (FIG. 2C) and together with the other monosaccharide composition data indicated that XAX1 transferred β-(1, 2) xylose onto α-(1,3) arabinose. Glycosidic linkage analysis of extracted xylan from XAX1 confirmed a 61% decrease in arabinofuranose residues substituted at O-2 and a concomitant 55% increase in terminal arabinose when compared to wild type, consistent with changes expected from the absence in XAX1 of arabinofuranose residues substituted at the O-2 position with xylose. The β-Xyl-α-Ara residues are a common substitution in grass xylan and have often been found with ferulic acid esters attached to the arabinose residues (12-16).

Figure 3:
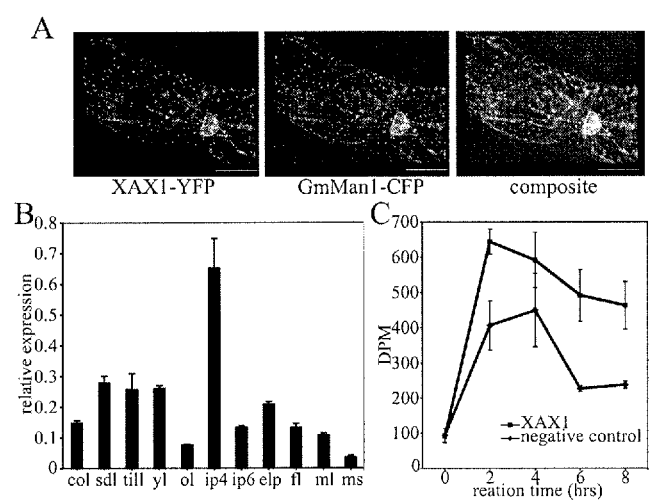
FIG. 3. Characterization of XAX1 protein localization and function. (A) Subcellular localization of fluorescently tagged XAX1 proteins. Confocal imaging (40×) of onion epidermal cells expressing, XAX1-YFP and GmMan1-CFP, the α-mannosidae Golgi marker. Scale bar is 50 µm. (B) Relative expression of XAXT in wild type rice. Key: col=coleoptile, sdl=7 dpg seedling, till=30 dpg tiller, yl=30 dpg young leaf, ol=30 dpg old leaf, ip4=immature panicle of 4 cm, ip6=developing panicle of 6 cm, elp=emerging panicle, fl=flag leaf, ml=mature leaf, ms=mature stem. (C) Xylosyltransferase activity reaction products. UDP-[$^{14}$C] Xylose incorporation to microsomes with an endogenous acceptor. Negative control is leaves infiltrated without XAX1 and represents the endogenous xylosyltransferase activity. Error bars are SEM with n=3 biological reps.

XAX1 is a Golgi-Localized Protein Specifically Expressed in Young Tissue, and has Xylosyltransferase Activity To confirm the proposed xylosyltransferase activity of the XAX1 protein, we isolated microsomes from leaves of *Nicotiana benthamiana* transiently expressing XAX1 and measured xylose incorporation onto endogenous acceptors in the presence of UDP-$^{14}$C-xylose. Peak activity was measured at 2H for XAX1 microsomes and 4H for endogenous XylT activity (FIG. 3C). Overall, XAX1 microsomes showed a 62% increase in XylT activity over the endogenously measured activity. To confirm that endogenous xylose-4-epimerase activity was not a significant factor in the results, we hydrolyzed the endogenous product to monosaccharide units and then separated the monosaccharides by TLC to determine radioactivity corresponding to xylose and arabinose. We found that the primary activity was from incorporation of xylose and that incorporation of arabinose was less than 20% of the total activity (FIG. 6D). GT activity studies in mung bean microsomes also found the epimerase activity to have a minimal effect on glucosyltransferase assays with UDP-arabinose (32).

Figure 4:
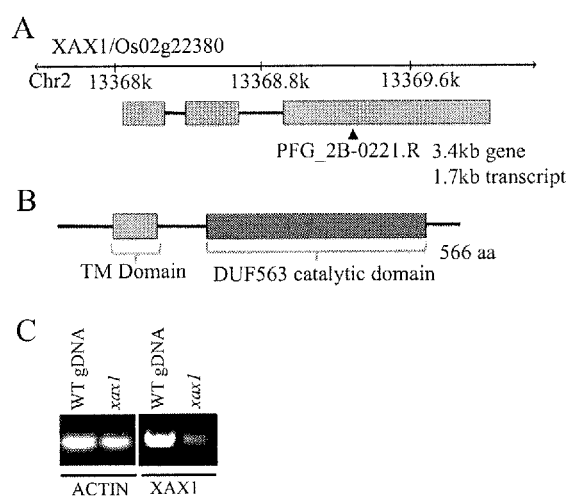
FIG. 4. XAX1 T-DNA insertional rice mutant. (A) Location of the T-DNA insertion. Image modified from RiceGE. (B) Protein structure of XAX1: N-terminal transmembrane domain and C-terminal DUF563 domain characteristic of GT61 family genes. (C) Confirmation of XAX1 knock out. Segregating wild type plants were used as negative control.

XAX1 is primarily expressed in younger tissue, including seedlings 7 days post germination (dpg) and has the highest expression in the immature panicle, and the lowest expression in mature stems and older leaves (FIG. 3B). In rice, xylan is abundant in both the primary and secondary cell walls. We wanted to determine if XAX1 localizes with other previously characterized xylan synthesis enzymes in the Golgi apparatus (33). As with other members of the GT61 family, XAX1 has an N-terminal putative transmembrane domain (FIG. 4B). To determine cellular localization, the XAX1 protein was fused to a C-terminal YFP and transiently expressed in onion cells. XAX1 co-localized with the GmMan1-CFP, the α-mannosidase I cis-Golgi marker (FIG. 3A), indicating that XAX1 is localized where xylan is known to be synthesized.

Absence of Xylose Substitution Improves Saccharification

Figure 5:
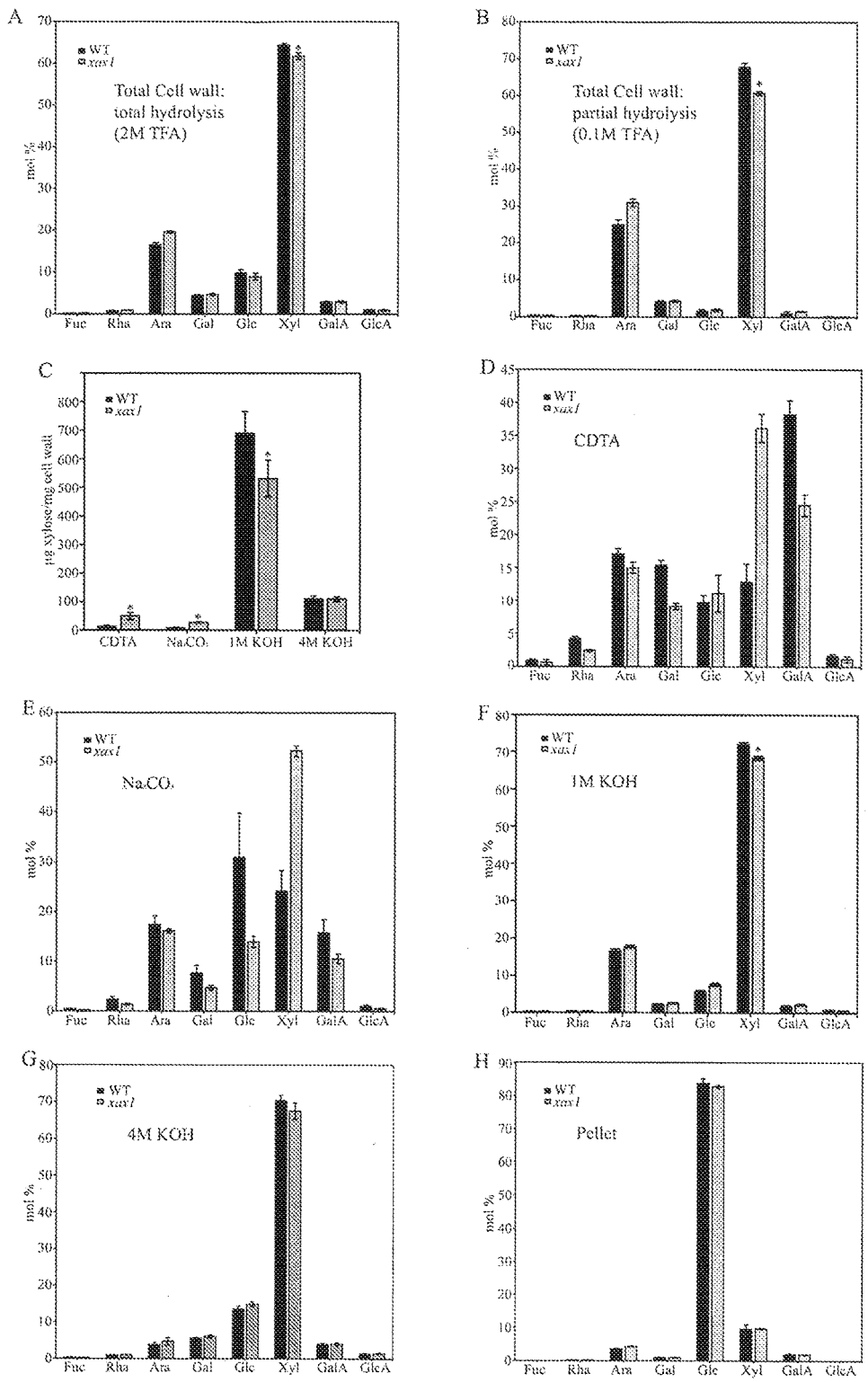
FIG. 5. Cell wall composition analysis. (A) Total sugar composition with total TFA hydrolysis with sugar separation and quantification on the HPAEC (B) Total sugar composition with 0.1% TFA partial hydrolysis (C) Cellular fractionation: CDTA fraction (D) Na$_2$CO$_3$ fraction (E) 1M KOH fraction (F) Sulfuric acid treatment of pellet (G) Saccharification assay and DNS quantification of sugars using an enzyme mixture of cellulases and α-mannosidases. Error bars represent SD (n=4).

Cell walls from the XAX1 mutant exhibited a 62% increase in the total sugars released compared to wild type after a 24-h treatment with an enzyme cocktail (Ctec2, Novozymes, Denmark) that contained cellulase, β-glucosidase, and hemicellulase (FIG. 1D). The cellulose content of the mutant was the same as wild type (FIG. 5F), and size exclusion chromatography found no difference in the size of the xylan molecules (FIG. 6A), which indicates that the increased extractability is not due to increased carbohydrate content in the mutant. Additionally, CDTA and $Na_2CO_3$ fractions, which in wild type contains mostly pectin sugars, showed that the xylose was more easily extracted in the mutant, also indicating a more easily extractable hemicellulose (FIGS. 5 C and D). The improved saccharification may be due to a decrease in the diferulic cross-links (34-36) or because a more easily extracted xylan allows cellulase enzymes better access to cellulose (37).

Discussion

Evolution of a Grass Specific Xylan Substitution

XAX1 is a member of glycosyltransferase family GT61, and we have shown it to be essential for the grass specific β-(1,2) xylose substitution of α-(1,3) arabinosyl residues, a disaccharide substitution on the xylan chain that is unique to grasses. The GT61 family was recently identified through bioinformatic analysis to be highly grass-diverged (28, 29, 38). Enzymes are grouped into the GT61 family based on a transmembrane domain and a DUF563 protein sequence (CAZy database (39), FIG. 4B). We found a single DUF563 sequence in the brown algae E. siliculosus, which suggests that this family originated around the time brown algae evolved or before; we used this brown algae sequence to root our GT61 tree. There are at least three distinct clades identifiable in the GT61 phylogenetic tree (clade A, B, and C). The basal plants are Physcomitrella patens and Selaginella moellendorffii), 13 genomes of dicosts are included and 4 genomes of grasses. The three clades are divided into (A, B, CI, CII, CIII, and CIV). XAX1 is located in the grass specific clade CIV. Clades A and B, which both include moss genes, are represented relatively evenly between grasses and dicots. Clade B genes have diverged far less than other genes in the family, and are generally represented by only a single sequence per genome (At5G5500 and Os08g39380 in Arabidopsis and rice respectively). One member of this clade, At5g55500 has been previously characterized to have β-(1, 2) xylosyltransferase activity, transferring xylose to N-linked glycans (40). There is nothing yet known about clade A, but it does contain five Selaginella representatives. We found Selaginella leaves to have no detectable arabinose on its xylan (FIG. 6E), and propose that this clade does not contain arabinosyl transferases involved in xylan biosynthesis. Most likely, clade A has a function similar to clade B or an as yet uncharacterized function. However, clade C, which contains Os02g22380 (XAX1), is dramatically expanded in the grasses, which is particularly true for groups III and IV in clade C, which have no known dicot orthologues. The recently characterized α-(1,3) arabinosyltransferases are part of clade Cland II. Clade CII contains the only dicot orthologues of clade C (27). Arabinose substitutions on xylan are abundant in grasses, but not unique to them. While O-3 substituted arabinose is characteristic of the grasses, many dicot species have O-2 substituted arabinose, and flax and psyllium seed mucilage have been shown to contain α-(1,2) α-(1,3) disubstituted or α-(1,3) monosubstituted arabinose on xylan, respectively (41, 42). Thus, having dicot orthologues in clade CII is not surprising. That XAX1 is located in the grass-unique clade CIV, appears correct, since the disaccharide substitution is a grass specific trait in xylan and associated with ferulate esters, which are also unique to grass xylans.

The Role of XAX1 in the Context of Ferulic Acid Esters

The decreased content in ferulate and coumarate esters in the XAX1 mutant is interesting and somewhat unexpected. It is not clear how hydroxycinnamate esters are added to xylan, but it is known to take place in the Golgi, and there is evidence that acyltransferases belonging to the BAHD family are involved (16, 43). The BAHD enzymes are cytoplasmic, suggesting that they do not directly ferulate xylan, but adds ferulic acid to an intermediate. A likely intermediate that has been proposed is UDP-arabinofuranose (44), which is also synthesized in the cytoplasm— again somewhat surprisingly since the precursor, UDP-arabinopyranose, is largely synthesized inside the Golgi lumen (45). However, if UDP-feruloyl-arabinose were the substrate for feruloylation of xylan, we would not expect to see a decrease in ferulate ester content in XAX1. The decreased hydroxycinnamate in the mutant suggests that ferulic acid is added subsequently to the addition of xylose to the un-feruloylated arabinose residues. In that case, the intermediate for feruloylation would be another as yet unidentified compound. Alternatively, hydroxycinnamates attached to arabinose in XAX1 are more susceptible to being removed by ferulic acid esterases. If the latter is the case, it would suggest a role of β-1,2-xylose substitutions on grass xylans in stabilizing the ferulic acid esters.

Rice Xylan Lacking β-(1,2) Xyl Substitution have Improved Release of Sugars

Mutant XAX1 plants exhibit an increased saccharification efficiency (FIG. 1D) and an increased extractability of xylan (FIGS. 5 C and D), most likely due to the lower ferulic cross-links (FIG. 1C), but it may also be due to increased solubility of the hemicelluloses and hence possible increased access of cellulases to cellulose. There does appear to be a slight increase in arabinose substitutions (FIG. 1B) possibly as a compensatory mechanism due to the XAX1 mutation. Based on the linkage analysis, there is an increase in di-substituted xylose (2,3,4-Xyl) presumably with α-(1,2) and α-(1,3) arabinose. This increase in arabinose would account for a degree of the increased extractability of xylan, but we propose that while this ~10% increase in arabinose may account for a fraction of the 62% increase in saccharification efficiency, it most likely does not account for the majority of the increased saccharification observed in XAX1. We find it more likely that the increased saccharification is largely a consequence of the 59% decrease in ferulic acid (FIG. 1C).

In conclusion, mutant XAX1 plants show a dwarfed phenotype and increased extractability that demonstrates the importance of the β-1,2-xylose substitutions on arabinoxylan. These findings also provide us with new insights into xylan synthesis and a unique capability to modify ferulic cross-links with a glycosyltransferase. As ferulic cross-links inhibit sugar release as well as microbial fermentation, this is a potentially important biotechnological tool for grass biofuel feedstocks.

Materials and Methods

Details of plant material, reagents, quantitative RT-PCR, microscopy, construction of GT61 phylogeny, LC-TOF Mass Spectrometry, and primers are described in SI Materials and Methods.

AIR Preparation and Analysis

AIR was prepared and analyzed with a high-performance anion-exchange chromatography with pulsed amperometric detection (HPAEC-PAD) as described (18) and in the SI Materials and Methods. The phenolic extraction of AIR was performed as described (46) and in the SI Materials and Methods. For the saccharification assay, 5 mg destarched AIR was autoclaved at 120° C. for 1 h. A 500-μl enzyme mixture containing 50 mM citrate buffer pH 6.2, 1.6% tetracycline, 2 μl Ctec2 enzyme mixture (Novozymes, Denmark), which contains cellulases, β-glucosidases, and hemicellulase was added and incubated at 50° C. for 24 h with shaking. After enzyme treatment, samples were pelleted, and released sugars in the supernatant were measured using DNS reagent (1% w/v 3,5-dinitrosalicylic acid, 30% w/v potassium sodium tartrate, 400 mM NaOH) reading absorbance at 540 nm.

Cell Wall Fractionation and Xylan Composition Analysis

Xylan was extracted from AIR as previously described (47) and in the SI Materials and Methods. Extracted xylan (1 mg/ml) was incubated with 1 U endoxylanase (Megazyme, Bray, Ireland) in 0.05 M ammonium acetate buffer (pH 6) at 42° C. for 24 h. The reaction mixture was heated at 100° C. for 10 min to stop the reaction and centrifuged prior to HPAEC analysis. The endoxylanse treated extract was incubated with 0.25 U α-L arabinofuranosidase from $A.$ $niger$ (Megazyme, Bray, Ireland) in 0.05 M sodium acetate buffer (pH 4) at 42° C. for 1 h. The reaction was stopped by boiling at 100° C. for 10 min and centrifuged. The released oligosaccharides after enzymatic digestion were separated by HPAEC on a Dionex DX 600 system equipped with a pulsed amperometric detector (PAD). A CarboPac PA200 column (3×250 mm) eluted with a gradient of 0-250 mM sodium acetate in 100 mM NaOH over 40 min at 0.4 ml/min was used. Xylose, arabinose and xylooligosaccharides (xylobiose, xylotriose, xylotetraose, xylopentaose and xylohexaose) (Megazyme, Bray, Ireland) were run as standards.

XylT Activity Assay

Infiltration of 4 week-old $N.$ $benthamiana$ leaves was done using $Agrobacterium$ tumefasciens strain C58 (OD=1), following the method described in (48). For details on the plasmid constructs, see the SI Materials and Methods. Leaves were collected 5 days after infiltration, flash frozen, ground in a mortar and pestle in 15 mL of buffer (50 mM HEPES pH 7.0, 400 mM sucrose, 1 mM PMSF, 1% w/v PVPP, Protease Inhibitor Cocktail). This was then filtered through Miracloth mesh and centrifuged at 3,000×g for 10 min. The supernatant was then centrifuged at 50,000×g for 1 h. (Beckman Ultracentrifuge). The pellets containing the microsomes were resuspended in a 50 mM HEPES pH 7.0, 400 mM sucrose buffer and stored at −80° C. Protein concentration was determined using the Bradford method. Microsomes corresponding to 100 μg protein were incubated with 50 mM HEPES pH 7.0, 400 mM sucrose, 5 mM MnCl2, 20 nli UDP-[$^{14}$C]Xylose (American Radiolabeled Chemicals, Inc., St. Louis, Mo., USA) in a total reaction volume of 50 μL. After incubation at 24° C. for various times, reaction was stopped by adding 70% ice-cold ethanol and 100 μg dextran as a carrier. The products were precipitated with ice-cold 70% ethanol and washed until no counts were found in the wash solution. Then the pellet was re-suspended in water, an equal volume of scintillation fluid was added (National Diagnostics), and the amount of activity was determined using scintillation counter set to measure $^{14}$C counts for 2 min (Beckman LS 6500).

Supplemental Materials and Methods

Growth of Plants.

Rice plants were grown in the summer at 30° C. in day and 24° C. at night, 60-80% relative humidity in the UC Davis greenhouses. T-DNA insertion lines were obtained from the Postech rice T-DNA insertion library in Korea. Mutant lines were genotyped using primers designed to be just outside each insertion site as well as an insertion internal primer. $N.$ $benthamiana$ plants were grown for 4 weeks at 24° C. with 12 h light (70 μmol photons m$^{-2}$ s$^{-1}$) and 60% humidity.

Expression Analysis.

Total RNA was extracted using the RNeasy plant mini kit (Qiagen, Valencia, Calif.) following manufacturer's instructions. RNA preparations were treated with DNase1 (Qiagen, Valencia, Calif.) to remove traces of DNA contamination. 1 μg of RNA was used for reverse transcription with the Transcriptor high fidelity cDNA synthesis kit (Roche) and oligo dT primers. After synthesis, the cDNA reaction was diluted four times in RNAse-free water, and 2 μl was used for PCR using the Fast SYBR Green master mix (Applied Biosystems, Carlsbad, Calif.) and gene-specific primers in a StepONE plus Q-PCR machine (Applied Biosystems).

Cell Wall Isolation and Monosaccharide Composition Analysis.

For rice mutants, 5-week old leaf tissue was collected, frozen in liquid nitrogen and freeze-dried overnight using a lyophilizer. Alcohol Insoluble Residue (AIR) preparation and destarching was done according to methods described in (1). For monosaccharide composition analysis, 5 mg was hydrolyzed in 15% trifluoroacetic acid at 120° C. for 1 h. The released monosaccharides were separated by HPAEC on a Dionex ICS3000 system (Sunnyvale, Calif.) equipped with a pulsed amperometric detector (PAD) as described (2).

Sequential Extraction of Xylan.

Xylan was extracted from AIR as previously described (3). AIR (5 mg) was suspended in 0.5 ml 0.05 M CDTA (pH 6.5) for 24 h at room temperature on thermomixer. The suspension was centrifuged at 48,000×g at 4° C. and the pellet washed twice with deionized water. The pellet was subsequently extracted using 0.05 M Na$_2$CO$_3$ containing 0.01 M NaBH$_4$ for 24 h at 4° C., washed twice with deionized water, and then 1M KOH, then 4M KOH for 24 h each at room temperature with shaking on thermomixer. The 1M KOH and 4M KOH fractions were similarly centrifuged at 48,000×g at 4° C. The KOH fractions were adjusted to pH 5 with glacial acetic acid. The fraction was further dialyzed against deionized water and then lyophilized.

Extraction, Separation and Quantification of Hydroxycinnamates.

For hydroxycinnamate extraction of plant material, 5 mg destarched AIR was saponified in 2M sodium hydroxide at 22° C. for 24 h in 10-ml Teflon tubes at room temperature on a rocking agitator. After acidification with 0.8 ml concentrated hydrochloric acid samples were extracted 3 times in ethyl acetate. The combined supernatants were vacuum dried and solubilized in 50% (v/v) methanol. HPLC separation was done as described (4) with a gradient of solvent A (0.2% TFA) and solvent B (acetonitrile): 0-5 min, 10% B isocratic; 5-25 min, 10-30% B linear; 25-40 min, 30% B isocratic; 40-45 min, 30-35% B linear; 45-46 min, 35-100% B linear; 46-51 min, 100% B isocratic; 51-53 min 100-10% B linear; 53-60 min 10% B isocratic.

Saccharification Assay.

To determine the amount of sugars released from plant material, water was added to 5 mg destarched AIR and the mixture was autoclaved at 120° C. for 1 h. A 500-μl enzyme mixture containing 50 mM citrate buffer pH 6.2, 1.6% tetracycline, 2 μl Ctec2 enzyme mixture (Novozymes, Denmark), which contains cellulases, β-glucosidases, and hemicellulase was added and incubated at 50° C. for 24 h with shaking. After enzyme treatment, samples were pelleted, and released sugars in the supernatant were measured using DNS reagent (1% w/v 3,5-dinitrosalicylic acid, 30% w/v potassium sodium tartrate, 400 mM NaOH) reading absorbance at 540 nm.

Enzyme Treatment of Cell Wall Extracts.

Xylan extracted from cell walls (1 mg/ml) were incubated with 1 U endoxylanase (Megazyme, Bray, Ireland) in 0.05 M ammonium acetate buffer (pH 6) at 42° C. for 24 h. The reaction mixture was heated at 100° C. for 10 min to stop the reaction and centrifuged prior to HPAEC analysis. The endoxylanse treated extract was incubated with 0.25 U α-L arabinofuranosidase from *A. niger* (Megazyme) in 0.05 M sodium acetate buffer (pH 4) at 42° C. for 1 h. The reaction was stopped by boiling at 100° C. for 10 min and centrifuged.

Xylan Fingerprinting by HPAEC.

The released oligosaccharides after enzymatic digestion were separated by HPAEC on a Dionex DX 600 system equipped with a pulsed amperometric detector (PAD). A CarboPac PA200 column (3×250 mm) eluted with a gradient of 0-250 mM sodium acetate in 100 mM NaOH over 40 min at 0.4 ml/min was used. Xylose, arabinose and xylooligosaccharides (xylobiose, xylotriose, xylotetraose, xylopentaose and xylohexaose) (Megazyme, Bray, Ireland) were run as standards.

LC-TOF Mass Spectrometry of 'Peak 1'.

The separation of metabolites was conducted on a Fermentation monitoring HPX-87H column with 8% cross linkage (150 mm length, 7.8 mm internal diameter, and 9 μm particle size; Bio-Rad, CA, USA) using an Agilent Technologies 1100 Series HPLC system. A sample injection volume of 10 μL was used throughout. The temperature of the sample tray was maintained at 4° C. by an Agilent FC/ALS Thermostat. The column compartment was set to 50° C. Metabolites were eluted isocratically with a mobile phase composition 0.1% formic acid. A flow rate of 0.5 ml min$^{-1}$ was used throughout. Xylobiose, xylotriose, xylotetraose, xylopentaose and xylohexaose (Megazyme, Bray, Ireland) were run as standards.

The HPLC system was coupled to an Agilent Technologies 6210 time-of-flight mass spectrometer (LC-TOF MS), by a ⅕ post-column split (Agilent Technologies, CA, USA). Nitrogen gas was used as both the nebulizing and drying gases to facilitate the production of gas-phase ions. The drying and nebulizing gases were set to 12 L/min and 30 psi, respectively, and a drying gas temperature of 330° C. was used throughout. Electrospray ionization (ESI) was conducted in the positive ion mode and a capillary voltage of 3500 V was utilized. MS experiments were carried out in the full scan mode, at 0.86 spectra/s, for the detection of [M+Na]$^+$ ions. The instrument was tuned for a range of 50-1700 m/z. Prior to LC-TOF MS analysis, the TOF MS was calibrated via an ESI-L-low concentration tuning mix (Agilent Technologies, CA, USA). Data acquisition and processing were performed by the MassHunter software package.

Transient Expression of XAX1 in *Nicotiana benthamiana*.

Infiltration of 4 week-old *N. benthamiana* leaves was done using *Agrobacterium* tumefasciens strain C58 (OD=1), following the method described in (1). For details on the plasmid constructs, see the SI Text. Leaves were collected 5 days post infiltration for protein isolation.

Microsomal Extraction of *N. Benthamiana* Leaves.

For protein isolation, leaves were flash frozen, ground in a mortar and pestle in 15 mL of buffer (50 mM HEPES pH 7.0, 400 mM sucrose, 1 mM PMSF, 1% w/v PVPP, Protease Inhibitor Cocktail). This was then filtered through Miracloth mesh and centrifuged at 3,000×g for 10 min. The supernatant was then centrifuged at 50,000×g for 1 h. (Beckman Ultracentrifuge). The pellets containing the microsomes were resuspended in a 50 mM HEPES pH 7.0, 400 mM sucrose buffer and stored at −80° C. Protein concentration was determined using the Bradford method.

Endogenous Activity Assay.

Microsomes corresponding to 100 μg protein were incubated with 50 mM HEPES pH 7.0, 400 mM sucrose, 5 mM MnCl$_2$, 740 Bq UDP-[$^{14}$C]Xylose (American Radiolabeled Chemicals, Inc., St. Louis, Mo., USA) in a total reaction volume of 50 μL. After incubation at 24° C. for various times, reaction was stopped by adding 70% ice-cold ethanol and 100 μg dextran as a carrier. The products were precipitated with ice-cold 70% ethanol and washed until no counts were found in the wash solution. Then the pellet was re-suspended in water, an equal volume of scintillation fluid was added (National Diagnostics), and the amount of activity was determined using scintillation counter set to measure $^{14}$C counts for 2 min (Beckman LS 6500).

Subcellular Localization of Fluorescent Tagged Proteins.

For the onion bombardments, the XAX1 pENTR clone without a stop codon was recombined into pBullet GW-YFP G-CFP, a customized bombardment vector containing a Gateway recombination site fused to a C-terminal YFP and a GmMan1::CFP, the α-mannosidae I cis-Golgi marker from *Glycine max* (5). Vectors were used to bombard onion peels using a PDS-1000 particle bombardment system (Bio-Rad). Prior to bombardment, onions peels were placed on agar plates containing 0.5× Murashige and Skoog medium and 2% sucrose for 1 hour at 22° C. to recover. Approximately 1 μg of plasmid DNA was used to coat 50 μl of 60 mg/ml, 1 μm gold particles (Bio-Rad) in the presence of 20 mM CaCl$_2$ and 0.8 mM spermidine for three minutes with mild vortexing. Particles were dehydrated with three ethanol washes and transferred onto plastic discs to dry. Particles were accelerated into onion peels by a burst of helium at 1100 psi under 28 in/Hg vacuum. Plates containing bombarded onions were covered in foil and incubated at 22° C. for 22 hours before being visualized by confocal microscopy. Transformed samples were analyzed using a Zeiss LSM710 meta (QUASAR detector) equipped with a 408 nm diode, argon and In tune laser. Images were taken using the inverted scope with a 1.30NA oil 40× objective. Samples were tagged with CFP and YFP were fixed with formaldehyde and imaged sequentially. The Zen software package (Carl Zeiss Inc.) was used for image acquisition and image analysis. The individual frames from 20 images were Z stacked.

Glycosidic Linkage Analysis.

Xylan was extracted from destarched AIR (5 mg) with 4M KOH and 10 mM NaBH$_4$ (1 ml) for 4 hours with vigorous shaking at room temperature. The insoluble residue was pelleted by centrifugation for 10 min at 21,000×g. The supernatant was neutralized with concentrated HCl and xylan was precipitated by adding water (4 ml) and 95% aqueous ethanol (14.5 ml) and incubating at −20 C overnight. After centrifugation at 3,200×g for 10 min the pellet was washed twice with 1 mL 70% ethanol before drying. The methylation procedure modified from the method described by Ciucanu 1984 (6). In brief, the pellet was partially dissolved in a suspension of dry DMSO and NaOH (12.5 mg/ml) and 100 μL methyliodide was added twice, with three hours stirring following the first addition and one hour following the second. Water (2 ml) was added to quench the reactions and dichloromethane (2 ml) was used to extract the partially methylated carbohydrates. The residue remaining after evaporation of the dichloromethane was hydrolyzed with 2M trifluoroacetic acid (TFA) at 121° C. for 90 minutes. The TFA was removed by evaporation under nitrogen and the pellet was reduced and acetylated as described (7). The residue was then extracted with 1.2 ml ethyl acetate and 5 ml water. The organic fraction was dried and the partially methylated alditol acetates were dissolved in acetone for GC-MS analysis with a 7890A GC system and a 5975C MS detector (Agilent) in EI mode. An SP-2380 column (Supelco) was used for the separation.

Mass Distribution Analysis.

Destarched alcohol insoluble residue (AIR) was incubated in 1 M KOH, 1% NaBH$_4$ (30 mg/ml) for 3 h with 1400 rpm shaking at RT. The supernatant was collected after centrifugation for 10 min at 12,000×g. The supernatant was neutralized using glacial acetic acid. After neutralization the supernatant was centrifuged for 10 min. at 12,000×g and the mass distribution resulting supernatant was analyzed as described (4). Equal amounts of sugar were loaded onto the SEC column.

Construction of GT61 Phylogeny.

GT61 family sequences in rice and *Arabidopsis* were determined based on a sequence possessing a DUF563 domain as well as a predicted transmembrane domain. To identify other family members, the completed genomes of 4 grass species (*B. distachyon, O. sativa, S. bicolor,* and *S. italica*), 13 dicot species (*A. coerulea, A. lyrata, A. thaliana, C. papaya, C. sativa, G. max, M. esculenta, M guttatus, M truncatula, P. persica, P. trichocarpa, R. communis,* and *V. vinifera*), the moss *P. patens* and lycophyte *S. moellendorffii* were clustered to the GT61 sequences from *Arabidopsis* and rice at 50% sequence identity using the program uCLUST (8). An alignment of all family members was constructed with MUSCLE (9), and this alignment was used to construct a maximum likelihood phylogeny with PhyML3 (10). The resulting tree was visualized using the tools available from the online resource interactive Tree Of Life (iTOL) (11).

REFERENCES

References Cited by Number

1. Ebringerova A & Heinze T (2000) Xylan and xylan derivatives—biopolymers with valuable properties, 1. Naturally occurring xylans structures, isolation procedures and properties. *Macromol. Rapid Commun.* 21:542-556.
2. Vinkx C J A & Delcour J A (1996) Rye (*Secale cereale* L.) arabinoxylans: A critical review. *Journal of Cereal Science* 24:1-14.
3. Klein-Marcuschamer D, Holmes B, Simmons B A, & Blanch H W (2011) Biofuel Economics. *Plant Biomass Conversion*, eds Hood E, Powell R, & P. N (John Wiley & Sons, New York), 1 Ed, pp 329-348
4. Scheller H V & Ulvskov P (2010) Hemicelluloses. *Annual Review of Plant Biology* 61(1):263-289.
5. Grabber J H, Ralph J, & Hatfield R D (2000) Cross-linking of maize walls by ferulate dimerization and incorporation into lignin. *J. Agric. Food Chem.* 48(12):6106-6113.
6. Himmel M E, Ding, Shi-You, Johnson, David K., Adney, William S., Nimlos, Mark R., Brady, John W., and Foust, Thomas D. (2007) Biomass recalcitrance: Engineering plants and enzymes for biofuels production. *Science* 315 (5813):804-807.
7. Grabber J H (2005) How do lignin composition, structure, and cross-linking affect degradability? A review of cell wall model studies. *Crop Science* 45:820-831.
8. Ebringerová A, Hromádková Z, & Heinze T (2005) Hemicellulose. *Advances in Polymer Science* 186:1-67.
9. Johansson M H & Samuelson O (1977) Reducing end groups in birch xylan and their alkaline degradation. *Wood Science and Technology* 11(251-263).
10. Andersson S I, Samuelson O, Ishihara M, & Shimizu K (1983) Structure of the reducing end-groups in spruce xylan. *Carbohydr Res.* 111:283-288.
11. Peña M J, et al. (2007) *Arabidopsis* irregular xylem8 and irregular xylem9: Implications for the complexity of glucuronoxylan biosynthesis. *Plant Cell* 19:549-563.
12. Wende G & Fry S C (1997) 2-O-β-D-xylopyranosyl-(5-O-feruloyl)-L-arabinose, a widespread component of grass cell walls. *Phytochemistry* 44:1019-1030.
13. Kusakabe I, Ohgushi, S., Yasui, T. and Kobayashi, T. (1983) Structures of the arabinoxylo-oligosaccharides from the hydrolytic products of corncob arabinoxylan by a xylanase from *Streptomyces. Agric. Biol. Chem.* 47(12): 2713-2723.
14. Yui T, Imada K, Shibuya N, & Ogawa K (1995) Conformation of an arabinoxylan isolated from the rice endosperm cell wall by X-ray diffraction and a conformational analysis. *Biosci. Biotech. Biochem* 59(6):965-968.
15. Hoije A, Sandstrom, Corine, Roubroeks, Johannes P., Andersson, Roger, Gohil, Suresh, Gatenholm, Paul (2006) Evidence of the presence of 2-O-β-d-xylopyranosyl-α-1-arabinofuranose side chains in barley husk arabinoxylan. *Carbohydr Res.* 341(18):2959-2966.
16. Obel N, Porchia A C, & Scheller H V (2003) Intracellular feruloylation of arabinoxylan in wheat: evidence for feruloyl-glucose as precursor. *Planta* 216(4):620-629.
17. Persson S, et al. (2007) The *Arabidopsis* irregular xylem8 mutant is deficient in glucuronoxylan and homogalacturonan, which are essential for secondary cell wall integrity. *Plant Cell* 19(1):237-255.
18. Brown D M, et al. (2007) Comparison of five xylan synthesis mutants reveals new insight into the mechanisms of xylan synthesis. *Plant Journal* 52:1154-1168.
19. Geisler-Lee J, et al. (2007) A predicted interactome for *Arabidopsis. Plant Physiology* 145:317-329.
20. Brown D M, Zhang Z N, Stephens E, Dupree P, & Turner S R (2009) Characterization of IRX10 and IRX10-like reveals an essential role in glucuronoxylan biosynthesis in *Arabidopsis. Plant Journal* 57(4):732-746.
21. Wu A M, et al. (2009) The *Arabidopsis* IRX10 and IRX10-LIKE glycosyltransferases are critical for glucuronoxylan biosynthesis during secondary cell wall formation. *Plant Journal* 57(4):718-731.
22. Chen X, et al. (2012) The OsIRX10 glycosyltransferase is critical for xylan biosynthesis in rice. *Plant Physiology* Submitted.
23. Lee C, Zhong, R, Richardson, E, Himmelsbach, D, McPhail, B, and Ye, Z H (2007) The PARVUS gene is expressed in cells undergoing secondary wall thickening and is essential for glucuronoxylan biosynthesis. *Plant Cell Physiology* 48:1659-1672.
24. Liepman A H, Wightman R, Geshi N, Turner S R, & Scheller H V (2010) *Arabidopsis*—a powerful model system for plant cell wall research. *Plant J* 61(6):1107-1121.
25. Mortimer J C, et al. (2010) Absence of branches from xylan in *Arabidopsis* gux mutants reveals potential for simplification of lignocellulosic biomass. *PNAS* 107(40): 17409-17414.
26. Oikawa A, et al. (2010) An integrative approach to the identification of *Arabidopsis* and rice genes involved in xylan and secondary wall development. *PLoS One* 5(11): e15481.

27. Anders N, et al. (2012) Glycosyl transferases in family 61 mediate arabinofuranosyl transfer onto xylan in grasses. *PNAS* 109(3):989-993.
28. Cao P J, Bartley L E, Jung K H, & Ronald P C (2008) Construction of a rice glycosyltransferase phylogenomic database and identification of rice-diverged glycosyltransferases. *Molecular Plant* 1(5):858-877.
29. Mitchell R A C, Dupree P, & Shewry P R (2007) A novel bioinformatics approach identifies candidate genes for the synthesis and feruloylation of arabinoxylan. *Plant Physiology* 144:43-53.
30. Ingelbrecht J A, Verwimp T, & Delcour J A (2000) Endoxylanases in durum wheat semolina processing: Solubilization of arabinoxylans, action of endogenous inhibitors, and effects on rheological properties. *J. Agric. Food Chem.* 48:2017-2022.
31. Kaneko S, Ishii T, Kobayashi H, & Kusakabe I (1998) Substrate specificities of α-L-arabinofuranosidases produced by two species of *Aspergillus niger. Biosci. Biotechnol. Biochem* 62(4):695-699.
32. Nunan K J & Scheller H V (2003) Solubilization of an arabinan arabinosyltransferase activity from mung bean hypocotyls. *Plant Physiology* 132(1):331-342.
33. Porchia A C, Sorensen S O, & Scheller H V (2002) Arabinoxylan biosynthesis in wheat. Characterization of arabinosyltransferase activity in Golgi membranes. *Plant Physiology* 130(1):432-441.
34. Buanafina M M, Langdon T, Hauck B, Dalton S J, & Morris P (2009) Manipulating the phenolic acid content and digestibility of Italian ryegrass (*Lolium multiflorum*) by vacuolar-targeted expression of a fungal ferulic acid esterase. *Appl. Biochem. Biotechnol.* 130:416-426.
35. Buanafina M M, Langdon T, Hauck B, Dalton S, & Morris P (2008) Expression of a fungal ferulic acid esterase increases cell wall digestibility of tall fescue (*Festuca arundinacea*). *Plant Biotechnology* 6:264-280.
36. Lam T B T, Iiyama K, & Stone B A (2003) Hot alkali-labile linkages in the walls of the forage grass *Phalaris aquatica* and *Lolium perenne* and their relation to in vitro wall digestibility. *Phytochemistry* 64(2):603-607.
37. Kumar R & Wyman C E (2009) Effect of xylanase supplementation of cellulase on digestion of corn stover solids prepared by leading pretreatment technologies. *Bioresource Technology* 100(18):4203-4213.
38. Vogel J P (2010) Genome sequencing and analysis of the model grass Brachypodium distachyon. *Nature* 463 (7282):763-768.
39. Cantarel B L, et al. (2009) The Carbohydrate-Active EnZymes database (CAZy): an expert resource for glycogenomics. *Nucleic Acids Res.* 37 (Database issue): D233-238.
40. Strasser R, et al. (2000) Molecular cloning and functional expression of beta1, 2-xylosyltransferase cDNA from *Arabidopsis thaliana. FEBS Letters* 472(1):105-108.
41. Darvill J E, McNeil M, Darvill A G, & Albersheim P (1980) Structure of plant cell walls. XI. Glucuronoarabinoxylan, a second hemicellulose in the primary cell walls of suspension-cultured sycamore cells. *Plant Physiology* 66:1135-1139.
42. Naran R, Chen G, & Carpita N C (2008) Novel rhamnogalacturonan I and arabinoxylan polysaccharides of flax seed mucilage. *Plant Physiology* 148:132-141.
43. Piston F, et al. (2010) Down-regulation of four putative arabinoxylan feruloyl transferase genes from family PF02458 reduces ester-linked ferulate content in rice cell walls. *Planta* 231:677-691.
44. Buanafina M M (2009) Feruloylation in grasses: Current and future perspectives. *Molecular Plant* 2(5861-872).
45. Rautengarten C, et al. (2011) The interconversion of UDP-arabinopyranose and UDP-arabinofuranose is indispensable for plant development in *Arabidopsis. Plant Cell* 23(4):1373-1390.
46. Rautengarten C, et al. (2011) The *Arabidopsis* Deficient in Cutin Ferulate (DCF) Encodes a Transferase Required for Feruloylation of ω-Hydroxyfatty Acids in Cutin Polyester. *Plant Physiology* at the http site world wide web entry plantphysiol.org/content/early/2011/12/08/pp. 111.187187.long.
47. Harholt J, et al. (2006) ARABINAN DEFICIENT1 is a putative arabinosyltransferase involved in biosynthesis of pectic arabinan in *Arabidopsis. Plant Physiology* 140:49-58.
48. Yin L, et al. (2011) The Cooperative Activities of CSLD2, CSLD3, and CSLD5 Are Required for Normal *Arabidopsis* Development. *Molecular Plant* 4(6):1024-1037.

REFERENCES CITED BY NUMBER IN SPECIFICATION SUPPLEMENTAL MATERIAL AND METHODS SECTION

1. Yin L, et al. (2011) The Cooperative Activities of CSLD2, CSLD3, and CSLD5 Are Required for Normal *Arabidopsis* Development. *Molecular Plant* 4(6):1024-1037.
2. Brown D M, et al. (2007) Comparison of five xylan synthesis mutants reveals new insight into the mechanisms of xylan synthesis. *Plant Journal* 52:1154-1168.
3. Harholt J, et al. (2006) ARABINAN DEFICIENT1 is a putative arabinosyltransferase involved in biosynthesis of pectic arabinan in *Arabidopsis. Plant Physiology* 140:49-58.
4. Harholt J, et al. (2010) Generation of transgenic wheat (*Triticum aestivum* L.) accumulating heterologous endoxylanase or ferulic acid esterase in the endosperm. *Plant Biotechnology Journal* 8(3):351-362.
5. Nelson B K, Cai X, & Nebenführ A (2007) A multicolored set of in vivo organelle markers for co-localization studies in *Arabidopsis* and other plants. *Plant Journal* 51:1126-1136.
6. Ciucanu I, Kerek, F. (1984) A Simple and repaid method for the permethylation of carbohydrates. *Carbohydrate Research* 131:209-217.
7. York W S, Darvill A G, McNeil M, & Albersheim P (1985) 3-deoxy-d-manno-2-octulosonic acid (KDO) is a component of rhamnogalacturonan II, a pectic polysaccharide in the primary cell walls of plants. *Carbohydrate Research* 135:109-126.
8. Edgar R C (2010) Search and clustering orders of magnitude faster than BLAST. *Bioinformatics* 26(19):2460-2461.
9. Edgar R C (2004) MUSCLE: multiple sequence alignment with high accuracy and high throughput. *Nucleic Acids Research* 32 (5):1792-1797.
10. Guindon S & Gascuel O (2003) A Simple, Fast, and Accurate Algorithm to Estimate Large Phylogenies by Maximum Likelihood. *Systematic Biology* 52(5):696-704.
11. Letunic I & Bork P (2007) Interactive Tree Of Life (iTOL): an online tool for phylogenetic tree display and annotation. *Bioinformatics* 23(1):127-128.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

| EXAMPLES OF SEQUENCES |
|---|
| SEQ ID NO: 1<br>Rice XAX1 cDNA sequence CDS length: 1701 nucleotides<br>ATGACGTCGACGGCGTACTCCCGGCCGTCGAAGCTGCCGGGCGGCGGCAACGGCAGCGAC<br>CGCAGGCTGCCGCCGCGGCTGATGAGGGGCCTCACCACCAAGATCGAGCCCAAGAAGCTC<br>GGCGTCGGCCTCCTCGCCGGCTGCTGCCTCGCGCTCCTCACCTACGTCTCCCTTGCCAAG<br>CTCTTCGCAATCTACTCCCCTGTGTTCGCCAGCACAGCCAACACATCCGCTCTGATGCAG<br>AACTCGCCGCCATCCTCGCCGGAGACGGGACCCATTCCGCCCCAAGAAACTGCAGCTGGC<br>GCCGGAAACAATGACAGCACTGTGGACCCCGTCGATCTCCCTGAGGACAAGTCGCTGGTG<br>GAGGCGCAGCCTCAAGAACCCGGCTTCCCCTCGGCGGAATCTCAGGAGCCTGGCTTGCCG<br>GCGGCGCTCTCGAGGAAGGAGGATGATGCGGAGAGGGCGGCGGCGGCGGCGGCCTCGGAG<br>ATAAAGCAATCCGAGAAGAAGAACGGCGTGGCGGCGGGTGGTGATACCAAGATAAAGTGC<br>GACGAGAACGGCGTGGACGAGGGCTTCCCGTACGCGCGGCCGTCGGTTTGCGAGCTGTAC<br>GGCGACGTCCGCGTCAGCCCCAAGCAGAAGACCATTTACGTCGTGAACCCGTCGGGCGCC<br>GGCGGCTTCGACGAGAACGGCGAGAAGCGGCTCCGGCCCTACGCCCGCAAGGACGATTTC<br>CTCCTCCCGGGCGTGGTGGAGGTGACTATCAAGTCCGTGCCCTCCGAGGCGGCGGCCCCC<br>AAGTGCACGAAGCAGCACGCCGTCCCCGCCGTGGTGTTCTCCGTGGCCGGGTACACGGAC<br>AACTTCTTCCACGACATGACCGATGCCATGATCCCGCTATTCCTGACGACGGCGCACCTC<br>AAGGGCGAGGTCCAGATCCTCATCACCAACTACAAGCCGTGGTGGGTGCAGAAGTACACG<br>CCGCTGCTCCGCAAGCTGTCCAACTACGACGTCATCAACTTCGACGAGGACGCCGGCGTG<br>CACTGCTTCCCGCAGGGGTACCTCGGTCTGTACCGCGACCGCGACCTCATCATCTCCCCG<br>CACCCGACCCGCAACCCGCGCAACTACACCATGGTGGACTACAACCGCTTCCTCCGCGAC<br>GCTCTGGAGCTCCGGCGCGACCGCCCGTCGGTGCTGGGCGAGGAGCCCGGGATGCGGCCG<br>CGGATGCTGATCATCTCCCGCGCCGGCACGCGCAAGCTGCTGAACCTCGAGGAGGTGGCC<br>GCGGCCGCGACGGAGCTTGGTTTCAACGTGACGGTGGCGGAGGCCGGTGCTGACGTGCCC<br>GCGTTCGCGGCGCTGGTGAACTCGGCGGACGTGCTGCTGGCCGTGCACGGCGCCGGGCTG<br>ACGAACCAGATCTTCCTCCCGGCGGAGGCCGTGGTGGTGCAGATCGTGCCGTGGGGGAAC<br>ATGGACTGGATGGCGACCAACTTTTACGGGCAGCCGGCGAGGGACATGCAGCTCCGGTAC<br>GTGGAGTACTACGTCGGCGAGGAGGAGACGAGCCTGAAGCACAACTACTCGCGAGATCAC<br>ATGGTGTTCAAGGACCCCAAGGCGCTCCACGCACAGGGATGGCAGACACTCGCCGCGACT<br>ATCATGAAGCAGGACGTCGAGGTCAACCTCACCAGGTTCCGGCCAATCCTGCTGCAGGCG<br>CTCGACAGGCTGCAGCAGTAA<br><br>SEQ ID NO: 2<br>Os02g22380.1 Rice XAX1 protein sequence: 566 amino acids<br>MTSTAYSRPSKLPGGGNGSDRRLPPRLMRGLTTKIEPKKLGVGLLAGCCLALLTYVSLAK<br>LFAIYSPVFASTANTSALMQNSPPSSPETGPIPPQETAAGAGNNDSTVDPVDLPEDKSLV<br>EAQPQEPGFPSAESQEPGLPAALSRKEDDAERAAAAAASEIKQSEKKNGVAAGGDTKIKC<br>DENGVDEGFPYARPSVCELYGDVRVSPKQKTIYVVNPSGAGGFDENGEKRLRPYARKDDF<br>LLPGVVEVTIKSVPSEAAAPKCTKQHAVPAVVFSVAGYTDNFFHDMTDAMIPLFLTTAHL<br>KGEVQILITNYKPWWVQKYTPLLRKLSNYDVINFDEDAGVHCFPQGYLGLYRDRDLIISP<br>HPTRNPRNYTMVDYNRFLRDALELRRDRPSVLGEEPGMRPRMLIISRAGTRKLLNLEEVA<br>AAATELGFNVTVAEAGADVPAFAALVNSADVLLAVHGAGLTNQIFLPAEAVVVQIVPWGN<br>MDWMATNFYGQPARDMQLRYVEYYVGEEETSLKHNYSRDHMVFKDPKALHAQGWQTLAAT<br>IMKQDVEVNLTRFRPILLQALDRLQQ*<br><br>SEQ ID NO: 3<br>Os02g22380 Rice XAX1 genomic DNA sequence<br>CCCATCCTCACCGATCTCTCTAAACCCAAATACGCAACAAATACTCAATCGTCACATCTT<br>AAAAAACAAAGAAAAAGGAAGAGAGAGAGAGAGGGAAAACAAAAAAGAAAAGAAAAATCA<br>ATTCCCAACCTTGCTGCTACAAATGCCTCAGGCTTAGCAACTCGACCTCCTCCCCCCTTC<br>TCCCCTTCCTCCCTTCTTTGACTTCCCCTTTCCTCCTCCGTGCGCACGCTCTCCTGATTC<br>ATACAGCATTTCGTCGGGGATGACGTCGACGGCGTACTCCCGGCCGTCGAAGCTGCCGGG<br>CGGCGGCAACGGCAGCGACCGCAGGCTGCCGCCGCGGCTGATGAGGGGCCTCACCACCAA<br>GATCGAGCCCAAGAAGCTCGGCGTCGGCCTCCTCGCCGGCTGCTGCCTCGCGCTCCTCAC<br>CTACGTCTCCCTTGCCAAGCTCTTCGCAATCTACTCCCCTGTGTTCGGTGCGTGCTCCCC<br>TAATCCCGATCCGCCCTAGGAGCTTACTTTTGGTTAAATCCCCTCCCGCGTTGTCTCTCG<br>AATCCAATCCATTTTGATTTAGTCTAATGGGAGCTGTTTTGAATCCGTTTTCAGCCAGCA<br>CAGCCAACACATCCGCTCTGATGCAGAACTCGCCGCCATCCTCGCCGGAGACGGGACCCA<br>TTCCGCCCCAAGAAACTGCAGCTGGCGCCGGAAACAATGACAGCACTGTGGACCCCGTCG<br>ATCTCCCTGAGGACAAGTCGCTGGTGGAGGCGCAGCCTCAAGAACCCGGCTTCCCCTCGG<br>CGGAATCTCAGGAGCCTGGCTTGCCGGCGGCGCTCTCGAGGAAGGAGGATGATGCGGAGA<br>GGGCGGCGGCGGCGGCCTCGGAGATAAAGCAATGTAAGGAAATCTTGCCTCTTTCTT<br>CCGCTCCCTTTTATTTGCGCACCTTTACTGGAAGGCAGAGCAAGCTACAGTAGAGCAAGT<br>CCCCAGTTGTTGTTGAGCGCAAGCAAGCAATCAATCTCGTTTGGATTTGGTAGAGACGCA<br>CGAGATCTGGGCGGTGTTTTATTGGGGATTTGATGGTAATTCAGTCTCGTTGGTTTGGTT<br>AATTCAGCCGAGAAGAAGAACGGCGTGGCGGCGGGTGGTGATACCAAGATAAAGTGCGAC<br>GAGAACGGCGTGGACGAGGGCTTCCCGTACGCGCGGCCGTCGGTTTGCGAGCTGTACGGC<br>GACGTCCGCGTCAGCCCCAAGCAGAAGACCATTTACGTCGTGAACCCGTCGGGCGCCGGC<br>GGCTTCGACGAGAACGGCGAGAAGCGGCTCCGGCCCTACGCCCGCAAGGACGATTTCCTC<br>CTCCCGGGCGTGGTGGAGGTGACTATCAAGTCCGTGCCCTCCGAGGCGGCGGCCCCCAAG<br>TGCACGAAGCAGCACGCCGTCCCCGCCGTGGTGTTCTCCGTGGCCGGGTACACGGACAAC<br>TTCTTCCACGACATGACCGATGCCATGATCCCGCTATTCCTGACGACGGCGCACCTCAAG<br>GGCGAGGTCCAGATCCTCATCACCAACTACAAGCCGTGGTGGGTGCAGAAGTACACGCCG |

EXAMPLES OF SEQUENCES

```
CTGCTCCGCAAGCTGTCCAACTACGACGTCATCAACTTCGACGAGGACGCCGGCGTGCAC
TGCTTCCCGCAGGGGTACCTCGGTCTGTACCGCGACCGCGACCTCATCATCTCCCCGCAC
CCGACCCGCAACCCGCGCAACTACACCATGGTGGACTACAACCGCTTCCTCCGCGACGCT
CTGGAGCTCCGGCGCGACCGCCCGTCGGTGCTGGGCGAGGAGCCCGGGATGCGGCCGCGG
ATGCTGATCATCTCCCGCGCCGGCACGCGCAAGCTGCTGAACCTCGAGGAGGTGGCCGCG
GCCGCGACGGAGCTTGGTTTCAACGTGACGGTGGCGGAGGCCGGTGCTGACGTGCCCGCG
TTCGCGGCGCTGGTGAACTCGGCGGACGTGCTGCTGGCCGTGCACGGCGCCGGGCTGACG
AACCAGATCTTCCTCCCGGCGGAGGCCGTGGTGGTGCAGATCGTGCCGTGGGGGAACATG
GACTGGATGGCGACCAACTTTTACGGGCAGCCGGCGAGGGACATGCAGCTCCGGTACGTG
GAGTACTACGTCGGCGAGGAGGAGACGAGCCTGAAGCACAACTACTCGCGAGATCACATG
GTGTTCAAGGACCCCAAGGCGCTCCACGCACAGGGATGGCAGACACTCGCCGCGACTATC
ATGAAGCAGGACGTCGAGGTCAACCTCACCAGGTTCCGGCCAATCCTGCTGCAGGCGCTC
GACAGGCTGCAGCAGTAACTCGTCTATCCCAATAATCGCAGGCAGCTCATGGCACACATC
AATGTATATGCCGGACGAGACGACACGACGAGGAACAAGACGGATACTAGTATATTGT
ACTGCTGCTTGAAAGAGATGATGATGATCTTAACCGGAGGAGAACCATCAGTTGTTGGCG
AGGCGGTGGAAGCTTTTCGCATATTGGTAATTGGTTGGGTTGTCCATTTTGGGTTTGTAA
CAATTTGCATAGGCATTACACACCAAAGATGTTCGATTTTTTTGTTCTTCTTACACTTCT
TCACTTCGCCAGCCCATTCAACACTATACATTCTTTTCTACTAATACGGAGCCAAACTAA
ACTATGGTGTTTAATTATTAAAACATCAAATTGGTCACCCAAACAAAACAAAGTGGCGAT
GAAAGAAAGATCCAAATCTGAGAGTTGTTTCAGACATGTGCAATCTCCTCTAATAAATTG
AACAAATGGTTGTTAAACGAATCTGCATCCCGAGCGTTGAAGGGGCTTAGCTGGTGCGGA
CGTGCCAGCATGGAAGTGTTCGTGGAGAAGGAAAATGGATTCGATGCTCTGTCCAACACT
GGTGAACTGCTGTATATGCACCCGCCTGCTGCCTGCTTTCAGCTTAAGGAAAAGATCACT
AATAATTGAAAAGCACAGGCTAACTAACCGGGCTCTGCAAGAAAGCTGTGACAGGTAAGT
CGTAACTAGTTTTGGGCAATCGAATACCTTCTCTCTTTTCTTCTCTTTTCTTGAGAGGCA
GACAGGGAGATATAGAGAAAGACCTTCTCCTTTTATCTTTATTTTTTCTTTTTTCCTAGA
ACCTTCTTGCTGTCTTTTGGTAGGGAAAGAGACTAGAAAATGGACAGTGATGATGAATGCAT
GAATTTCCCATAAGAAATTGGCAAGCTAGCCTCACCTTTTCAGTATCGTATGCATCACGC
GAAAAGATTAATCACAAGAGGGTGACCCGGCAACGAGAAGAGGGATCAGCCAAGACAAT
CTTGTAGCCGTTAGTATGAAACACACGATTAATCACAAGCCACGCCATGCTCTTCATGC
```

SEQ ID NO: 4 Glade 4 Bradi4g27360.1_(B. distachyon) Brachypodium distachyon Glade 4 (XAX1) amino acid sequence
MASTAYTRPSKPPGLAGERRPAARLSRELGRIEPKKLGIGLVAGCCLALLTYISFARLFAIYSPVFESTS
LVMKNAPPASTAVPSTESGTVQQKIELEDEKDVVEDPKEPSFPEEERKVEEKEEETAVTKPSGGGDAAET
KIICDENGVDEGFPYARPSVCELTGDIRISPREKTMFFVTPSAAGAAALDANGEKKIRPYARKDTFLLPG
VVEVTIKSVPSAEAAPACTRQHDVPAVVFSVAGYTDNFFHDNTDVMIPLFLTTAHLRGEVQLLITNFKPW
WVKKFTPLLKKLSNYEVINFDKDEEVRCFRQGNLGLYRDRDLILSPHPTRNPRNYTMVDYNRFLRGAFGL
PRDAPAVLGEKTSARPKMLMIERKGTRKLLNLAAVVAMCEELGFAVTVAEAGADVRGFAETVNAADVLLA
VHGAGLTNQIFLPTGAVMVQIVPWGKMDWMATNFYGQPARDMQLRYVEYYVSEEETTLKDRFPRDHYVFK
DPMAIHAQGWPALADIVMKQDVMVNVTRFKPFLLSALDKLQE SEQ ID NO: 5 Sb10g018270.1_(S. bicolor) Sorghum Glade 4 (XAX1) amino
acid sequence
MASTAYSRPSKPPGPAAGERKGPRLAKELGRIEPKKLGIGLVAGCCLALLTYLSFARLFAIYSPVLDSSS
LLLKNTPPATTTVPATEALPVQQKTQVEDQKDAPDPELDPNMPNLPEVTQKDQQEAATATKPGAGAVTEAK
ITCDENGVDEGFPYARPPVCELAGDIRISPKEKAMYLVNPSGAGPFDSNGEKKIRPFARNDGFLLPGVVE
VTIKSVSSAAAAPQCTRRHDVPVVVFSVAGYTDNFFHDNTDVLIPLFLTTAHLKGEVQFLITNFKPWWVN
KFTPLLKKLSNYDVINFDEDKEVHCFRAGHLGMYRDRDLIISPHPTRNPHNYSMVDYNRFLRRAFSLPRD
APAVLGAETSAKPKMLIIERKGTRKLLNLREVAAMCEALGFAVTVAEAGADVRGFAERVNAADVLLAVHG
AGLTNQIFLPTGAVLVQIVPWGKMDWMATNFYGQPARDMRLRYVEYYVSEEETTLKDKYPRDHYVFKDPM
RIHAQGWPAIAEIIMKQDVMVNMTRFKPFLLKALDELQE SEQ ID NO: 6 Bradi3g11340.1_(B. distachyon)Brachypodium distachyon
Glade 4 (XAX1) amino acid sequence
MAGSQEPGLPEAVSRKDDAEKTAAAAEPKPKPSEENPEKSNVAAAVEGTAKANMTCDENGVDEGFPYARP
AVCELSGDIRVSPKQKTMYLVNPSGAATGFDEKGEKRLRPYARNDDFLLPGVVEVTVKSVPSTAAAPQCT
KQHRVPAVVFSVAGYTDNFFHDNTDALIPLYVTTAHLKGEVQLLITNYKPWWVQKYTPVLRKLSSYDVIN
FDEDAGVHCFHEGYLGLYRDRDLIISPHPTRNPRNYTMVDYNRFLRGVFELRRERPAVLGEEPGMRPRML
IISRSGTRKLLNLDEVAAEASELGFNVTVAEAGADVPAFAALVNSADVLLAVHGAGLTNQIFLPTDAVVL
QIVPWGNMDWQATNFYGQPAREMQLRYVEYYVGEEETSLKDKYPRDHMVFKDPKALHKQGWQTLANTIMK
QDVQVNITRFRPFLLQAIDKLQP SEQ ID NO: 7 Bradi1g06560.1_(B. distachyon) Brachypodium distachyon
Glade 4 (XAX1) amino acid sequence
MNSTAYSRPSKLPGGAGGERRPPRLMRGFAAKIEPKKLGAGLLAGCCLALLTYVSLAKLFAIYSPVFAST
ANTSGLLQNSPPSSSSVPETTDAIPAEATFVGRKNDDPAADPVDFPEEGPSMDGSQEPGLPEVVSRKEDD
AEKAIAATSQPKPSEEDSAAAGAGEGTPPAKMTCDENGVDEGFPYARPAVCELSGDIRVSPKDKTMYLVN
PSGAAAGFDENGEKRLRPYARKDEFLLPAVVEVTVKSVPSASGAPRCTKRHRVPAVVFSVAGYTDNFFHD
NTDALIPLFLTTAHLKGEVQLLITNYKPWWVQKYTPVLRKLSNYDVINFDDEDGAVHCFPDGYLGLYRD
RDLIISPHPTRNPRNYTMVDYNKFLRGALELPREKPAVLGEEPGMRPRMLIISRSGTRRLLNLDEVSAAA
SELGFNVTVAEAGGEADVPAFAAMVNSADVLLAVHGAGLTNQIFLPTNAVVLQIVPWGNMDWMATNFYGQ
PAREMQLRYVEYYVGEEETSLKDKYPRDHVVFRDPKALHTQGWETLADTIMKQDVQVDLSRFRPFLLQAI
DKLQE

| EXAMPLES OF SEQUENCES |
| --- |
| SEQ ID NO: 8 Sb04g000840.1_(*S. bicolor*) *Sorghum* Glade 4 (XAX1) amino acid sequence<br>MTSTAYSRSSKLPGGGPERRLPPRLMRSLTSKIEPKKLGVGLVAGCCLALLTYVSLAKLFAIYSPVFAST<br>ANTSALMQNAPPTSSKPSVPETETIPPQETFGGAGADPREAVTGSEEPGLPEAAVTRKDMAGSDEPGLPT<br>RKDDGDNAAAAEPTKPAAAAAAEDKKEGDDGNGGQGGGKMTCDENGVDEGFPYARPTVCELSGDVRVSPK<br>QKTVYLVNPSGAGGFDESGEKRLRPYARKDDFLMPGVTEVTVKSVPSAAVAPKCTKHHTVPAVLFSIAGY<br>TDNFFHDMVDAMVPLFLTTSHLKGEVQLLITNYKPWWVQKYTPLLRKMSLHDVINFDAEDADDVHCFPAG<br>AFVGLYRDRDLILSPHPTRNPRNLTMVDFSRFMRGALALPRDRPAVLGEAPGMRPRMLIISRAGTRRLLN<br>LDEVAKVADELGFNVTIAEAGADVPAFAAQVNAADVLVGVHGAGLANVVFLPTEAVVVQIVPWGKMDWMA<br>TNFYARPAAGMALRYLEYYVGEEETSLKDKYPRDHVVFRDPMSLHTQGWQALAQTIMKQDVAVNLTKFRP<br>VLLQALDKLQQ |

---

What is claimed is:

1. A method of improving the amount of soluble sugar obtained from rice plant biomass material, the method comprising:
   inhibiting endogenous XAX1 in a rice plant;
   determining that the rice plant has reduced levels of ferulic acid in the cell wall compared to a wildtype rice plant;
   selecting the rice plant;
   providing biomass material from the rice plant;
   performing a saccharification reaction; and
   obtaining soluble sugar at a level at least 10% higher than that obtained from a wildtype rice plant in which endogenous XAX1 gene expression is not inhibited.

2. A method of improving the amount of soluble sugar obtained from grass plant biomass material, the method comprising:
   deleting or mutating an endogenous XAX1 gene encoding amino acid SEQ ID NO:2; or deleting or mutating the promoter of the endogenous XAX1 gene, in a rice plant;
   determining that the rice plant has reduced levels of ferulic acid in the cell wall compared to a wildtype rice plant;
   selecting the rice plant;
   providing biomass material from the rice plant
   performing a saccharification reaction; and
   obtaining soluble sugar at a level at least 50% higher than that obtained from the wildtype rice plant that does not have the genetic alteration.

3. The method of claim 2, wherein the rice plant comprises an exogenous XAX1 gene encoding the amino acid sequence of SEQ ID NO:2 operably linked to a vessel-specific promoter.

4. The method of claim 2, wherein the endogenous XAX1 gene is knocked out.

5. The method of claim 2, wherein the endogenous XAX1 gene is deleted.

6. The method of claim 2, wherein the endogenous XAX1 gene is deleted.

7. The method of claim 2, wherein the endogenous XAX1 gene promoter is mutagenized.

8. The method of claim 2, wherein the rice plant has at least a 10% reduction in the level of hydroxycinnamate esters compared to a corresponding wildtype rice plant.

9. The method of claim 2, wherein the rice plant has at least a 10% reduction in lignin content in comparison to a corresponding wildtype rice plant.

10. The method of claim 1, wherein the rice plant is genetically modified to express a polynucleotide that encodes the amino acid sequence of SEQ ID NO:2 and the polynucleotide is operably linked to a vessel-specific promoter.

11. The method of claim 1, wherein the rice plant has at least a 10% reduction in the level of hydroxycinnamate esters compared to a corresponding wildtype rice plant.

12. The method of claim 1, wherein the plant has at least a 10% reduction in lignin content in comparison to a corresponding wildtype rice plant.

* * * * *

SEQUENCE LISTING

<160> NUMBER OF SEQ ID NOS: 8

<210> SEQ ID NO 1
<211> LENGTH: 1701
<212> TYPE: DNA
<213> ORGANISM: Oryza sativa
<220> FEATURE:
<223> OTHER INFORMATION: Oryza sativa Japonica Group cultivar Nipponbare
      rice xylosyl arabinosyl substitution of xylan 1 (XAX1) cDNA

<400> SEQUENCE: 1

```
atgacgtcga cggcgtactc ccggccgtcg aagctgccgg gcggcggcaa cggcagcgac      60
cgcaggctgc cgccgcggct gatgaggggc ctcaccacca agatcgagcc caagaagctc     120
ggcgtcggcc tcctcgccgg ctgctgcctc gcgctcctca cctacgtctc ccttgccaag     180
ctcttcgcaa tctactcccc tgtgttcgca agcacagcca acatccgc tctgatgcag       240 aactcgccgc catcctcgcc ggagacggga cccattccgc ccaagaaac tgcagctggc      300 gccggaaaca atgacagcac tgtggacccc gtcgatctcc ctgaggacaa gtcgctggtg     360
gaggcgcagc ctcaagaacc cggcttcccc tcggcggaat ctcaggagcc tggcttgccg     420
gcggcgctct cgaggaagga ggatgatgcg gagagggcgg cggcggcggc ggcctcggag     480
ataaagcaat ccgagaagaa gaacggcgtg gcggcgggtg gtgataccaa gataaagtgc     540
gacgagaacg gcgtggacga gggcttcccg tacgcgcggc cgtcggtttg cgagctgtac     600
ggcgacgtcc gcgtcagccc caagcagaag accatttacg tcgtgaaccc gtcgggcgcc     660
ggcggcttcg acgagaacgg cgagaagcgg ctccggccct acgcccgcaa ggacgatttc     720
ctcctcccgg gcgtggtgga ggtgactatc aagtccgtgc cctccgaggc ggcggccccc     780
aagtgcacga agcagcacgc cgtccccgcc gtggtgttct ccgtggccgg gtacacggac     840
aacttcttcc acgacatgac cgatgccatg atcccgctat cctgacgac ggcgcacctc     900 aagggcgagg tccagatcct catcaccaac tacaagccgt ggtgggtgca gaagtacacg     960
ccgctgctcc gcaagctgtc caactacgac gtcatcaact tcgacgagga cgccggcgtg    1020
cactgcttcc cgcaggggta cctcggtctg taccgcgacc gcgacctcat catctccccg    1080
cacccgaccc gcaaccgcgc caactacacc atggtggact acaaccgctt cctccgcgac    1140
gctctggagc tccggcgcga ccgcccgtcg gtgctgggcg aggagcccgg gatgcggccg    1200
cggatgctga tcatctcccg cgccggcacg cgcaagctgc tgaacctcga ggaggtggcc    1260
gcggccgcga cggagcttgg tttcaacgtg acggtggcgg aggccggtgc tgacgtgccc    1320
gcgttcgcgg cgctggtgaa ctcggcggac gtgctgctgg ccgtgcacgg cgccgggctg    1380
acgaaccaga tcttcctccc ggcggaggcc gtggtggtgc agatcgtgcc gtggggggaac   1440
```

```
atggactgga tggcgaccaa cttttacggg cagccggcga gggacatgca gctccggtac    1500
gtggagtact acgtcggcga ggaggagacg agcctgaagc acaactactc gcgagatcac    1560
atggtgttca aggaccccaa ggcgctccac gcacagggat ggcagacact cgccgcgact    1620
atcatgaagc aggacgtcga ggtcaacctc accaggttcc ggccaatcct gctgcaggcg    1680
ctcgacaggc tgcagcagta a                                              1701
```

<210> SEQ ID NO 2
<211> LENGTH: 566
<212> TYPE: PRT
<213> ORGANISM: Oryza sativa
<220> FEATURE:
<223> OTHER INFORMATION: Oryza sativa Japonica Group cultivar Nipponbare rice xylosyl arabinosyl substitution of xylan 1 (XAX1)

<400> SEQUENCE: 2

```
Met Thr Ser Thr Ala Tyr Ser Arg Pro Ser Lys Leu Pro Gly Gly Gly
 1               5                  10                  15

Asn Gly Ser Asp Arg Arg Leu Pro Pro Arg Leu Met Arg Gly Leu Thr
            20                  25                  30

Thr Lys Ile Glu Pro Lys Lys Leu Gly Val Gly Leu Leu Ala Gly Cys
        35                  40                  45

Cys Leu Ala Leu Leu Thr Tyr Val Ser Leu Ala Lys Leu Phe Ala Ile
    50                  55                  60

Tyr Ser Pro Val Phe Ala Ser Thr Ala Asn Thr Ser Ala Leu Met Gln
65                  70                  75                  80

Asn Ser Pro Pro Ser Pro Glu Thr Gly Pro Ile Pro Pro Gln Glu
            85                  90                  95

Thr Ala Ala Gly Ala Gly Asn Asn Asp Ser Thr Val Asp Pro Val Asp
            100                 105                 110

Leu Pro Glu Asp Lys Ser Leu Val Glu Ala Gln Pro Gln Glu Pro Gly
        115                 120                 125

Phe Pro Ser Ala Glu Ser Gln Glu Pro Gly Leu Pro Ala Ala Leu Ser
    130                 135                 140

Arg Lys Glu Asp Asp Ala Glu Arg Ala Ala Ala Ala Ala Ser Glu
145                 150                 155                 160

Ile Lys Gln Ser Glu Lys Lys Asn Gly Val Ala Ala Gly Gly Asp Thr
                165                 170                 175

Lys Ile Lys Cys Asp Glu Asn Gly Val Asp Glu Gly Phe Pro Tyr Ala
            180                 185                 190

Arg Pro Ser Val Cys Glu Leu Tyr Gly Asp Val Arg Val Ser Pro Lys
        195                 200                 205

Gln Lys Thr Ile Tyr Val Val Asn Pro Ser Gly Ala Gly Gly Phe Asp
    210                 215                 220

Glu Asn Gly Glu Lys Arg Leu Arg Pro Tyr Ala Arg Lys Asp Asp Phe
225                 230                 235                 240

Leu Leu Pro Gly Val Val Glu Val Thr Ile Lys Ser Val Pro Ser Glu
                245                 250                 255

Ala Ala Ala Pro Lys Cys Thr Lys Gln His Ala Val Pro Ala Val Val
            260                 265                 270

Phe Ser Val Ala Gly Tyr Thr Asp Asn Phe Phe His Asp Met Thr Asp
        275                 280                 285

Ala Met Ile Pro Leu Phe Leu Thr Thr Ala His Leu Lys Gly Glu Val
    290                 295                 300
```

```
Gln Ile Leu Ile Thr Asn Tyr Lys Pro Trp Trp Val Gln Lys Tyr Thr
305                 310                 315                 320

Pro Leu Leu Arg Lys Leu Ser Asn Tyr Asp Val Ile Asn Phe Asp Glu
                325                 330                 335

Asp Ala Gly Val His Cys Phe Pro Gln Gly Tyr Leu Gly Leu Tyr Arg
            340                 345                 350

Asp Arg Asp Leu Ile Ile Ser Pro His Pro Thr Arg Asn Pro Arg Asn
        355                 360                 365

Tyr Thr Met Val Asp Tyr Asn Arg Phe Leu Arg Asp Ala Leu Glu Leu
    370                 375                 380

Arg Arg Asp Arg Pro Ser Val Leu Gly Glu Glu Pro Gly Met Arg Pro
385                 390                 395                 400

Arg Met Leu Ile Ile Ser Arg Ala Gly Thr Arg Lys Leu Leu Asn Leu
                405                 410                 415

Glu Glu Val Ala Ala Ala Thr Glu Leu Gly Phe Asn Val Thr Val
            420                 425                 430

Ala Glu Ala Gly Ala Asp Val Pro Ala Phe Ala Ala Leu Val Asn Ser
        435                 440                 445

Ala Asp Val Leu Leu Ala Val His Gly Ala Gly Leu Thr Asn Gln Ile
    450                 455                 460

Phe Leu Pro Ala Glu Ala Val Val Gln Ile Val Pro Trp Gly Asn
465                 470                 475                 480

Met Asp Trp Met Ala Thr Asn Phe Tyr Gly Gln Pro Ala Arg Asp Met
                485                 490                 495

Gln Leu Arg Tyr Val Glu Tyr Tyr Val Gly Glu Glu Thr Ser Leu
            500                 505                 510

Lys His Asn Tyr Ser Arg Asp His Met Val Phe Lys Asp Pro Lys Ala
        515                 520                 525

Leu His Ala Gln Gly Trp Gln Thr Leu Ala Ala Thr Ile Met Lys Gln
    530                 535                 540

Asp Val Glu Val Asn Leu Thr Arg Phe Arg Pro Ile Leu Leu Gln Ala
545                 550                 555                 560

Leu Asp Arg Leu Gln Gln
                565

<210> SEQ ID NO 3
<211> LENGTH: 3359
<212> TYPE: DNA
<213> ORGANISM: Oryza sativa
<220> FEATURE:
<223> OTHER INFORMATION: Oryza sativa Japonica Group cultivar Nipponbare
      rice xylosyl arabinosyl substitution of xylan 1 (XAX1) genomic DNA

<400> SEQUENCE: 3
cccatcctca ccgatctctc taaacccaaa tacgcaacaa atactcaatc gtcacatctt      60
aaaaaacaaa gaaaaaggaa gagagagaga gagggaaaac aaaaaagaaa agaaaaatca    120
attcccaacc ttgctgctac aaatgcctca ggcttagcaa ctcgacctcc tccccccttc    180
tccccttcct cccttctttg acttccccctt tcctcctccg tgcgcacgct ctcctgattc    240
atacagcatt tcgtcgggga tgacgtcgac ggcgtactcc cggccgtcga agctgccggg    300
cggcggcaac ggcagcgacc gcaggctgcc gccgcggctg atgagggggcc tcaccaccaa    360 gatcgagccc aagaagctcg gcgtcggcct cctgccggc tgctgcctcg cgctcctcac    420
ctacgtctcc cttgccaagc tcttcgcaat ctactcccct gtgttcggtg cgtgctcccc    480
taatcccgat ccgccctagg agcttacttt tggttaaatc ccctcccgcg ttgtctctcg    540
```

-continued

```
aatccaatcc attttgattt agtctaatgg gagctgtttt gaatccgttt tcagccagca     600
cagccaacac atccgctctg atgcagaact cgccgccatc ctcgccggag acgggaccca     660
ttccgcccca agaaactgca gctggcgccg aaacaatgca cagcactgtg accccgtcg     720
atctccctga ggacaagtcg ctggtggagg cgcagcctca agaacccggc ttcccctcgg     780
cggaatctca ggagcctggc ttgccggcgg cgctctcgag gaaggaggat gatgcggaga     840
gggcggcggc ggcggcggcc tcggagataa agcaatgtaa ggaaatcttg cctctttctt     900
ccgctcccct ttatttgcgc acctttactg gaaggcagag caagctacag tagagcaagt     960
ccccagttgt tgttgagcgc aagcaagcaa tcaatctcgt ttggatttgg tagagacgca    1020
cgagatctgg gcggtgtttt attggggatt tgatggtaat tcagtctcgt tggtttggtt    1080
aattcagccg agaagaagaa cggcgtggcg gcgggtggtg ataccaagat aaagtgcgac    1140
gagaacggcg tggacgaggg cttcccgtac gcgcggccgt cggtttgcga gctgtacggc    1200
gacgtccgcg tcagccccaa gcagaagacc atttacgtcg tgaacccgtc gggcgccggc    1260
ggcttcgacg agaacggcga gaagcggctc cggccctacg cccgcaagga cgatttcctc    1320
ctcccgggcg tggtggaggt gactatcaag tccgtgccct ccgaggcggc ggcccccaag    1380
tgcacgaagc agcacgccgt ccccgccgtg gtgttctccg tggccgggta cacggacaac    1440
ttcttccacg acatgaccga tgccatgatc ccgctattcc tgacgacggc gcacctcaag    1500
ggcgaggtcc agatcctcat caccaactac aagccgtggt gggtgcagaa gtacacgccg    1560
ctgctccgca gctgtccaa ctacgacgtc atcaacttcg acgaggacgc cggcgtgcac    1620
tgcttcccgc aggggtacct cggtctgtac cgcgaccgcg acctcatcat ctccccgcac    1680
ccgacccgca acccgcgcaa ctacaccatg gtggactaca accgcttcct ccgcgacgct    1740
ctggagctcc ggcgcgaccg cccgtcggtg ctgggcgagg agcccgggat gcggccgcgg    1800
atgctgatca tctcccgcgc cggcacgcgc aagctgctga acctcgagga ggtggccgcg    1860
gccgcgacga agcttggttt caacgtgacg gtggcggagg ccggtgctga cgtgcccgcg    1920
ttcgcggcgc tggtgaactc ggcggacgtg ctgctggccg tgcacggcgc cgggctgacg    1980
aaccagatct tcctcccggc ggaggccgtg gtggtgcaga tcgtgccgtg ggggaacatg    2040
gactggatgg cgaccaactt ttacgggcag ccggcgaggg acatgcagct ccggtacgtg    2100
gagtactacg tcgcgaggga ggagacgagc ctgaagcaca actactcgcg agatcacatg    2160
gtgttcaagg accccaaggc gctccacgca cagggatggc agacactcgc cgcgactatc    2220
atgaagcagg acgtcgaggt caacctcacc aggttccggc caatcctgct gcaggcgctc    2280
gacaggctgc agcagtaact cgtctatccc aataatcgca ggcagctcat ggcacacatc    2340
aatgtatatg ccgggacgag acgacacgac gaggaacaag aacggatact agtatattgt    2400
actgctgctt gaaagagatg atgatgatct taaccggagg agaaccatca gttgttggcg    2460
aggcggtgga agcttttcgc atattggtaa ttggttgggt tgtccatttt gggtttgtaa    2520
caatttgcat aggcattaca caccaaagat gttcgatttt tttgttcttc ttacacttct    2580
tcacttcgcc agcccattca acactataca ttcttttcta ctaatacgga gccaaactaa    2640
actatggtgt ttaattatta aaacatcaaa ttggtcaccc aaacaaaaca aagtggcgat    2700
gaaagaaaga tccaaatctg agagttgttt cagacatgtg caatctcctc taataaattg    2760
aacaaatggt tgttaaacga atctgcatcc cgagcgttga aggggcttag ctggtgcgga    2820
cgtgccagca tggaagtgtt cgtggagaag gaaaatggat tcgatgctct gtccaacact    2880
ggtgaactgc tgtatatgca cccgcctgct gcctgctttc agcttaagga aaagatcact    2940
```

-continued

```
aataattgaa aagcacaggc taactaaccg ggctctgcaa gaaagctgtg acaggtaagt    3000
cgtaactagt tttgggcaat cgaataccTT ctctcttttc ttctcttttc ttgagaggca    3060
gacagggaga tatagagaaa gaccttctcc ttttatcttt attttttctt ttttcctaga    3120
accttcttgc tgtcttttgg tagggaaaga gactagaaaa tggaacgatg atgaatgcat    3180
gaatttccca taagaaattg gcaagctagc ctcaccTTTT cagtatcgta tgcatcacgc    3240
gaaaagatta atcacaagag ggtgacccgg caacgagaag aggagatcag ccaagacaat    3300
cttgtagccg ttagtatgaa acacacgatt aatcacaagc cacgccatgc tcttcatgc     3359
```

<210> SEQ ID NO 4
<211> LENGTH: 532
<212> TYPE: PRT
<213> ORGANISM: Brachypodium distachyon
<220> FEATURE:
<223> OTHER INFORMATION: Brachypodium distachyon strain Bd21 clade 4
      false brome Bradi4g27360.1 (XAX1)

<400> SEQUENCE: 4

```
Met Ala Ser Thr Ala Tyr Thr Arg Pro Ser Lys Pro Pro Gly Leu Ala
 1               5                  10                  15

Gly Glu Arg Arg Pro Ala Ala Arg Leu Ser Arg Glu Leu Gly Arg Ile
             20                  25                  30

Glu Pro Lys Lys Leu Gly Ile Gly Leu Val Ala Gly Cys Cys Leu Ala
         35                  40                  45

Leu Leu Thr Tyr Ile Ser Phe Ala Arg Leu Phe Ala Ile Tyr Ser Pro
     50                  55                  60

Val Phe Glu Ser Thr Ser Leu Val Met Lys Asn Ala Pro Pro Ala Ser
 65                  70                  75                  80

Thr Ala Val Pro Ser Thr Glu Ser Gly Thr Val Gln Gln Lys Ile Glu
                 85                  90                  95

Leu Glu Asp Glu Lys Asp Val Val Glu Asp Pro Lys Glu Pro Ser Phe
            100                 105                 110

Pro Glu Glu Glu Arg Lys Val Glu Glu Lys Glu Glu Thr Ala Val
        115                 120                 125

Thr Lys Pro Ser Gly Gly Gly Asp Ala Ala Glu Thr Lys Ile Ile Cys
    130                 135                 140

Asp Glu Asn Gly Val Asp Glu Gly Phe Pro Tyr Ala Arg Pro Ser Val
145                 150                 155                 160

Cys Glu Leu Thr Gly Asp Ile Arg Ile Ser Pro Arg Glu Lys Thr Met
                165                 170                 175

Phe Phe Val Thr Pro Ser Ala Ala Gly Ala Ala Ala Leu Asp Ala Asn
            180                 185                 190

Gly Glu Lys Lys Ile Arg Pro Tyr Ala Arg Lys Asp Thr Phe Leu Leu
        195                 200                 205

Pro Gly Val Val Glu Val Thr Ile Lys Ser Val Pro Ser Ala Glu Ala
    210                 215                 220

Ala Pro Ala Cys Thr Arg Gln His Asp Val Pro Ala Val Val Phe Ser
225                 230                 235                 240

Val Ala Gly Tyr Thr Asp Asn Phe Phe His Asp Asn Thr Asp Val Met
                245                 250                 255

Ile Pro Leu Phe Leu Thr Thr Ala His Leu Arg Gly Glu Val Gln Leu
            260                 265                 270

Leu Ile Thr Asn Phe Lys Pro Trp Trp Val Lys Lys Phe Thr Pro Leu
        275                 280                 285
```

```
Leu Lys Lys Leu Ser Asn Tyr Glu Val Ile Asn Phe Asp Lys Asp Glu
    290                 295                 300
Glu Val Arg Cys Phe Arg Gln Gly Asn Leu Gly Leu Tyr Arg Asp Arg
305                 310                 315                 320
Asp Leu Ile Leu Ser Pro His Pro Thr Arg Asn Pro Arg Asn Tyr Thr
                325                 330                 335
Met Val Asp Tyr Asn Arg Phe Leu Arg Gly Ala Phe Gly Leu Pro Arg
            340                 345                 350
Asp Ala Pro Ala Val Leu Gly Glu Lys Thr Ser Ala Arg Pro Lys Met
        355                 360                 365
Leu Met Ile Glu Arg Lys Gly Thr Arg Lys Leu Leu Asn Leu Ala Ala
    370                 375                 380
Val Val Ala Met Cys Glu Glu Leu Gly Phe Ala Val Thr Val Ala Glu
385                 390                 395                 400
Ala Gly Ala Asp Val Arg Gly Phe Ala Glu Thr Val Asn Ala Ala Asp
                405                 410                 415
Val Leu Leu Ala Val His Gly Ala Gly Leu Thr Asn Gln Ile Phe Leu
            420                 425                 430
Pro Thr Gly Ala Val Met Val Gln Ile Val Pro Trp Gly Lys Met Asp
        435                 440                 445
Trp Met Ala Thr Asn Phe Tyr Gly Gln Pro Ala Arg Asp Met Gln Leu
    450                 455                 460
Arg Tyr Val Glu Tyr Tyr Val Ser Glu Glu Thr Thr Leu Lys Asp
465                 470                 475                 480
Arg Phe Pro Arg Asp His Tyr Val Phe Lys Asp Pro Met Ala Ile His
                485                 490                 495
Ala Gln Gly Trp Pro Ala Leu Ala Asp Ile Val Met Lys Gln Asp Val
            500                 505                 510
Met Val Asn Val Thr Arg Phe Lys Pro Phe Leu Leu Ser Ala Leu Asp
        515                 520                 525
Lys Leu Gln Glu
    530

<210> SEQ ID NO 5
<211> LENGTH: 529
<212> TYPE: PRT
<213> ORGANISM: Sorghum bocolor
<220> FEATURE:
<223> OTHER INFORMATION: Sorghum bicolor cultivar BTx623 clade 4
      hypothetical protein, Sb10g018270.1, locus
      SORBIDRAFT_10g018270 (XAX1)

<400> SEQUENCE: 5

Met Ala Ser Thr Ala Tyr Ser Arg Pro Ser Lys Pro Pro Gly Pro Ala
1               5                   10                  15
Ala Gly Glu Arg Lys Gly Pro Arg Leu Ala Lys Glu Leu Gly Arg Ile
            20                  25                  30
Glu Pro Lys Lys Leu Gly Ile Gly Leu Val Ala Gly Cys Cys Leu Ala
        35                  40                  45
Leu Leu Thr Tyr Leu Ser Phe Ala Arg Leu Phe Ala Ile Tyr Ser Pro
    50                  55                  60
Val Leu Asp Ser Ser Ser Leu Leu Leu Lys Asn Thr Pro Pro Ala Thr
65                  70                  75                  80
Thr Thr Val Pro Ala Thr Glu Ala Leu Pro Val Gln Gln Lys Thr Gln
                85                  90                  95
```

```
Val Glu Asp Gln Lys Asp Ala Pro Asp Pro Glu Leu Asp Pro Asn Met
            100                 105                 110

Pro Asn Leu Pro Glu Val Thr Gln Lys Asp Gln Glu Ala Ala Thr
        115                 120                 125

Ala Thr Lys Pro Ala Gly Ala Val Thr Glu Ala Lys Ile Thr Cys Asp
        130                 135                 140

Glu Asn Gly Val Asp Glu Gly Phe Pro Tyr Ala Arg Pro Pro Val Cys
145                 150                 155                 160

Glu Leu Ala Gly Asp Ile Arg Ile Ser Pro Lys Glu Lys Ala Met Tyr
                165                 170                 175

Leu Val Asn Pro Ser Gly Ala Gly Pro Phe Asp Ser Asn Gly Glu Lys
            180                 185                 190

Lys Ile Arg Pro Phe Ala Arg Asn Asp Gly Phe Leu Leu Pro Gly Val
        195                 200                 205

Val Glu Val Thr Ile Lys Ser Val Ser Ala Ala Ala Pro Gln
            210                 215                 220

Cys Thr Arg Arg His Asp Val Pro Val Val Phe Ser Val Ala Gly
225                 230                 235                 240

Tyr Thr Asp Asn Phe Phe His Asp Asn Thr Asp Val Leu Ile Pro Leu
                245                 250                 255

Phe Leu Thr Thr Ala His Leu Lys Gly Glu Val Gln Phe Leu Ile Thr
            260                 265                 270

Asn Phe Lys Pro Trp Trp Val Asn Lys Phe Thr Pro Leu Leu Lys Lys
        275                 280                 285

Leu Ser Asn Tyr Asp Val Ile Asn Phe Asp Glu Asp Lys Glu Val His
        290                 295                 300

Cys Phe Arg Ala Gly His Leu Gly Met Tyr Arg Asp Arg Asp Leu Ile
305                 310                 315                 320

Ile Ser Pro His Pro Thr Arg Asn Pro His Asn Tyr Ser Met Val Asp
                325                 330                 335

Tyr Asn Arg Phe Leu Arg Arg Ala Phe Ser Leu Pro Arg Asp Ala Pro
            340                 345                 350

Ala Val Leu Gly Ala Glu Thr Ser Ala Lys Pro Lys Met Leu Ile Ile
            355                 360                 365

Glu Arg Lys Gly Thr Arg Lys Leu Leu Asn Leu Arg Glu Val Ala Ala
        370                 375                 380

Met Cys Glu Ala Leu Gly Phe Ala Val Thr Val Ala Glu Ala Gly Ala
385                 390                 395                 400

Asp Val Arg Gly Phe Ala Glu Arg Val Asn Ala Ala Asp Val Leu Leu
            405                 410                 415

Ala Val His Gly Ala Gly Leu Thr Asn Gln Ile Phe Leu Pro Thr Gly
            420                 425                 430

Ala Val Leu Val Gln Ile Val Pro Trp Gly Lys Met Asp Trp Met Ala
        435                 440                 445

Thr Asn Phe Tyr Gly Gln Pro Ala Arg Asp Met Arg Leu Arg Tyr Val
        450                 455                 460

Glu Tyr Tyr Val Ser Glu Glu Thr Thr Leu Lys Asp Lys Tyr Pro
465                 470                 475                 480

Arg Asp His Tyr Val Phe Lys Asp Pro Met Arg Ile His Ala Gln Gly
                485                 490                 495

Trp Pro Ala Ile Ala Glu Ile Ile Met Lys Gln Asp Val Met Val Asn
            500                 505                 510
```

```
Met Thr Arg Phe Lys Pro Phe Leu Leu Lys Ala Leu Asp Glu Leu Gln
            515                 520                 525

Glu

<210> SEQ ID NO 6
<211> LENGTH: 443
<212> TYPE: PRT
<213> ORGANISM: Brachypodium distachyon
<220> FEATURE:
<223> OTHER INFORMATION: Brachypodium distachyon strain Bd21 clade 4
      false brome Bradi3g11340.1 (XAX1)

<400> SEQUENCE: 6

Met Ala Gly Ser Gln Glu Pro Gly Leu Pro Glu Ala Val Ser Arg Lys
  1               5                  10                  15

Asp Asp Ala Glu Lys Thr Ala Ala Ala Glu Pro Lys Pro Lys Pro
                 20                  25                  30

Ser Glu Glu Asn Pro Glu Lys Ser Asn Val Ala Ala Val Glu Gly
         35                  40                  45

Thr Ala Lys Ala Asn Met Thr Cys Asp Glu Asn Gly Val Asp Glu Gly
 50                  55                  60

Phe Pro Tyr Ala Arg Pro Ala Val Cys Glu Leu Ser Gly Asp Ile Arg
 65                  70                  75                  80

Val Ser Pro Lys Gln Lys Thr Met Tyr Leu Val Asn Pro Ser Gly Ala
                 85                  90                  95

Ala Thr Gly Phe Asp Glu Lys Gly Glu Lys Arg Leu Arg Pro Tyr Ala
                100                 105                 110

Arg Asn Asp Asp Phe Leu Leu Pro Gly Val Val Glu Val Thr Val Lys
                115                 120                 125

Ser Val Pro Ser Thr Ala Ala Pro Gln Cys Thr Lys Gln His Arg
130                 135                 140

Val Pro Ala Val Val Phe Ser Val Ala Gly Tyr Thr Asp Asn Phe Phe
145                 150                 155                 160

His Asp Asn Thr Asp Ala Leu Ile Pro Leu Tyr Val Thr Thr Ala His
                165                 170                 175

Leu Lys Gly Glu Val Gln Leu Leu Ile Thr Asn Tyr Lys Pro Trp Trp
                180                 185                 190

Val Gln Lys Tyr Thr Pro Val Leu Arg Lys Leu Ser Ser Tyr Asp Val
                195                 200                 205

Ile Asn Phe Asp Glu Asp Ala Gly Val His Cys Phe His Glu Gly Tyr
                210                 215                 220

Leu Gly Leu Tyr Arg Asp Arg Asp Leu Ile Ile Ser Pro His Pro Thr
225                 230                 235                 240

Arg Asn Pro Arg Asn Tyr Thr Met Val Asp Tyr Asn Arg Phe Leu Arg
                245                 250                 255

Gly Val Phe Glu Leu Arg Arg Glu Arg Pro Ala Val Leu Gly Glu Glu
                260                 265                 270

Pro Gly Met Arg Pro Arg Met Leu Ile Ile Ser Arg Ser Gly Thr Arg
                275                 280                 285

Lys Leu Leu Asn Leu Asp Glu Val Ala Ala Glu Ala Ser Glu Leu Gly
                290                 295                 300

Phe Asn Val Thr Val Ala Glu Ala Gly Ala Asp Val Pro Ala Phe Ala
305                 310                 315                 320

Ala Leu Val Asn Ser Ala Asp Val Leu Leu Ala Val His Gly Ala Gly
                325                 330                 335
```

```
Leu Thr Asn Gln Ile Phe Leu Pro Thr Asp Ala Val Val Leu Gln Ile
                335                 340                 345                 350

Val Pro Trp Gly Asn Met Asp Trp Gln Ala Thr Asn Phe Tyr Gly Gln
            355                 360                 365

Pro Ala Arg Glu Met Gln Leu Arg Tyr Val Glu Tyr Val Gly Glu
        370                 375                 380

Glu Glu Thr Ser Leu Lys Asp Lys Tyr Pro Arg Asp His Met Val Phe
385                 390                 395                 400

Lys Asp Pro Lys Ala Leu His Lys Gln Gly Trp Gln Thr Leu Ala Asn
                405                 410                 415

Thr Ile Met Lys Gln Asp Val Gln Val Asn Ile Thr Arg Phe Arg Pro
            420                 425                 430

Phe Leu Leu Gln Ala Ile Asp Lys Leu Gln Pro
        435                 440
```

<210> SEQ ID NO 7
<211> LENGTH: 565
<212> TYPE: PRT
<213> ORGANISM: Brachypodium distachyon
<220> FEATURE:
<223> OTHER INFORMATION: Brachypodium distachyon strain Bd21 clade 4 false brome Bradi1g06560.1 (XAX1)

<400> SEQUENCE: 7

```
Met Asn Ser Thr Ala Tyr Ser Arg Pro Ser Lys Leu Pro Gly Gly Ala
1               5                   10                  15

Gly Gly Glu Arg Arg Pro Pro Arg Leu Met Arg Gly Phe Ala Ala Lys
            20                  25                  30

Ile Glu Pro Lys Lys Leu Gly Ala Gly Leu Leu Ala Gly Cys Cys Leu
        35                  40                  45

Ala Leu Leu Thr Tyr Val Ser Leu Ala Lys Leu Phe Ala Ile Tyr Ser
    50                  55                  60

Pro Val Phe Ala Ser Thr Ala Asn Thr Ser Gly Leu Leu Gln Asn Ser
65                  70                  75                  80

Pro Pro Ser Ser Ser Val Pro Glu Thr Thr Asp Ala Ile Pro Ala
                85                  90                  95

Glu Ala Thr Phe Val Gly Arg Lys Asn Asp Pro Ala Ala Asp Pro
            100                 105                 110

Val Asp Phe Pro Glu Glu Gly Pro Ser Met Asp Gly Ser Gln Glu Pro
        115                 120                 125

Gly Leu Pro Glu Val Val Ser Arg Lys Glu Asp Ala Glu Lys Ala
    130                 135                 140

Ile Ala Ala Thr Ser Gln Pro Lys Pro Ser Glu Glu Asp Ser Ala Ala
145                 150                 155                 160

Ala Gly Ala Gly Glu Gly Thr Pro Pro Ala Lys Met Thr Cys Asp Glu
                165                 170                 175

Asn Gly Val Asp Glu Gly Phe Pro Tyr Ala Arg Pro Ala Val Cys Glu
            180                 185                 190

Leu Ser Gly Asp Ile Arg Val Ser Pro Lys Asp Lys Thr Met Tyr Leu
        195                 200                 205

Val Asn Pro Ser Gly Ala Ala Gly Phe Asp Glu Asn Gly Glu Lys
    210                 215                 220

Arg Leu Arg Pro Tyr Ala Arg Lys Asp Glu Phe Leu Leu Pro Ala Val
225                 230                 235                 240

Val Glu Val Thr Val Lys Ser Val Pro Ser Ala Ser Gly Ala Pro Arg
                245                 250                 255
```

```
Cys Thr Lys Arg His Arg Val Pro Ala Val Val Phe Ser Val Ala Gly
            260                 265                 270

Tyr Thr Asp Asn Phe Phe His Asp Asn Thr Asp Ala Leu Ile Pro Leu
        275                 280                 285

Phe Leu Thr Thr Ala His Leu Lys Gly Glu Val Gln Leu Leu Ile Thr
    290                 295                 300

Asn Tyr Lys Pro Trp Trp Val Gln Lys Tyr Thr Pro Val Leu Arg Lys
305                 310                 315                 320

Leu Ser Asn Tyr Asp Val Ile Asn Phe Asp Glu Asp Gly Gly Ala
                325                 330                 335

Val His Cys Phe Pro Asp Gly Tyr Leu Gly Leu Tyr Arg Asp Arg Asp
            340                 345                 350

Leu Ile Ile Ser Pro His Pro Thr Arg Asn Pro Arg Asn Tyr Thr Met
                355                 360                 365

Val Asp Tyr Asn Lys Phe Leu Arg Gly Ala Leu Glu Leu Pro Arg Glu
        370                 375                 380

Lys Pro Ala Val Leu Gly Glu Glu Pro Gly Met Arg Pro Arg Met Leu
385                 390                 395                 400

Ile Ile Ser Arg Ser Gly Thr Arg Arg Leu Leu Asn Leu Asp Glu Val
                405                 410                 415

Ser Ala Ala Ser Glu Leu Gly Phe Asn Val Thr Val Ala Glu Ala
            420                 425                 430

Gly Gly Glu Ala Asp Val Pro Ala Phe Ala Ala Met Val Asn Ser Ala
                435                 440                 445

Asp Val Leu Leu Ala Val His Gly Ala Gly Leu Thr Asn Gln Ile Phe
    450                 455                 460

Leu Pro Thr Asn Ala Val Leu Gln Ile Val Pro Trp Gly Asn Met
465                 470                 475                 480

Asp Trp Met Ala Thr Asn Phe Tyr Gly Gln Pro Ala Arg Glu Met Gln
                485                 490                 495

Leu Arg Tyr Val Glu Tyr Tyr Val Gly Glu Glu Thr Ser Leu Lys
            500                 505                 510

Asp Lys Tyr Pro Arg Asp His Val Val Phe Arg Asp Pro Lys Ala Leu
                515                 520                 525

His Thr Gln Gly Trp Glu Thr Leu Ala Asp Thr Ile Met Lys Gln Asp
    530                 535                 540

Val Gln Val Asp Leu Ser Arg Phe Arg Pro Phe Leu Leu Gln Ala Ile
545                 550                 555                 560

Asp Lys Leu Gln Glu
                565

<210> SEQ ID NO 8
<211> LENGTH: 571
<212> TYPE: PRT
<213> ORGANISM: Sorghum bicolor
<220> FEATURE:
<223> OTHER INFORMATION: Sorghum bicolor cultivar BTx623 clade 4
      hypothetical protein, Sb04g000840.1, locus
      SORBIDRAFT_04g000840 (XAX1)

<400> SEQUENCE: 8

Met Thr Ser Thr Ala Tyr Ser Arg Ser Lys Leu Pro Gly Gly Gly
1               5                   10                  15

Pro Glu Arg Arg Leu Pro Pro Arg Leu Met Arg Ser Leu Thr Ser Lys
            20                  25                  30
```

-continued

```
Ile Glu Pro Lys Lys Leu Gly Val Gly Leu Val Ala Gly Cys Cys Leu
         35                  40                  45
Ala Leu Leu Thr Tyr Val Ser Leu Ala Lys Leu Phe Ala Ile Tyr Ser
 50                      55                  60
Pro Val Phe Ala Ser Thr Ala Asn Thr Ser Ala Leu Met Gln Asn Ala
 65                  70                  75                  80
Pro Pro Thr Ser Ser Lys Pro Ser Val Pro Glu Thr Glu Thr Ile Pro
                 85                  90                  95
Pro Gln Glu Thr Phe Gly Gly Ala Gly Ala Asp Pro Arg Glu Ala Val
             100                 105                 110
Thr Gly Ser Glu Glu Pro Gly Leu Pro Glu Ala Ala Val Thr Arg Lys
         115                 120                 125
Asp Met Ala Gly Ser Asp Glu Pro Gly Leu Pro Thr Arg Lys Asp Asp
     130                 135                 140
Gly Asp Asn Ala Ala Ala Glu Pro Thr Lys Pro Ala Ala Ala Ala
 145                 150                 155                 160
Ala Ala Glu Asp Lys Lys Glu Gly Asp Asp Gly Asn Gly Gly Gln Gly
                 165                 170                 175
Gly Gly Lys Met Thr Cys Asp Glu Asn Gly Val Asp Glu Gly Phe Pro
             180                 185                 190
Tyr Ala Arg Pro Thr Val Cys Glu Leu Ser Gly Asp Val Arg Val Ser
         195                 200                 205
Pro Lys Gln Lys Thr Val Tyr Leu Val Asn Pro Ser Gly Ala Gly Gly
     210                 215                 220
Phe Asp Glu Ser Gly Glu Lys Arg Leu Arg Pro Tyr Ala Arg Lys Asp
 225                 230                 235                 240
Asp Phe Leu Met Pro Gly Val Thr Glu Val Thr Val Lys Ser Val Pro
                 245                 250                 255
Ser Ala Ala Val Ala Pro Lys Cys Thr Lys His His Thr Val Pro Ala
             260                 265                 270
Val Leu Phe Ser Ile Ala Gly Tyr Thr Asp Asn Phe Phe His Asp Met
         275                 280                 285
Val Asp Ala Met Val Pro Leu Phe Leu Thr Thr Ser His Leu Lys Gly
     290                 295                 300
Glu Val Gln Leu Leu Ile Thr Asn Tyr Lys Pro Trp Trp Val Gln Lys
 305                 310                 315                 320
Tyr Thr Pro Leu Leu Arg Lys Met Ser Leu His Asp Val Ile Asn Phe
                 325                 330                 335
Asp Ala Glu Asp Ala Asp Val His Cys Phe Pro Ala Gly Ala Phe
             340                 345                 350
Val Gly Leu Tyr Arg Asp Arg Asp Leu Ile Leu Ser Pro His Pro Thr
         355                 360                 365
Arg Asn Pro Arg Asn Leu Thr Met Val Asp Phe Ser Arg Phe Met Arg
     370                 375                 380
Gly Ala Leu Ala Leu Pro Arg Asp Arg Pro Ala Val Leu Gly Glu Ala
 385                 390                 395                 400
Pro Gly Met Arg Pro Arg Met Leu Ile Ile Ser Arg Ala Gly Thr Arg
                 405                 410                 415
Arg Leu Leu Asn Leu Asp Glu Val Ala Lys Val Ala Asp Glu Leu Gly
             420                 425                 430
Phe Asn Val Thr Ile Ala Glu Ala Gly Ala Asp Val Pro Ala Phe Ala
         435                 440                 445
```

-continued

```
Ala Gln Val Asn Ala Ala Asp Val Leu Val Gly Val His Gly Ala Gly
    450                 455                 460

Leu Ala Asn Val Val Phe Leu Pro Thr Glu Ala Val Val Val Gln Ile
465                 470                 475                 480

Val Pro Trp Gly Lys Met Asp Trp Met Ala Thr Asn Phe Tyr Ala Arg
                485                 490                 495

Pro Ala Ala Gly Met Ala Leu Arg Tyr Leu Glu Tyr Tyr Val Gly Glu
                500                 505                 510

Glu Glu Thr Ser Leu Lys Asp Lys Tyr Pro Arg Asp His Val Val Phe
            515                 520                 525

Arg Asp Pro Met Ser Leu His Thr Gln Gly Trp Gln Ala Leu Ala Gln
    530                 535                 540

Thr Ile Met Lys Gln Asp Val Ala Val Asn Leu Thr Lys Phe Arg Pro
545                 550                 555                 560

Val Leu Leu Gln Ala Leu Asp Lys Leu Gln Gln
                565                 570
```